US009763899B2

(12) United States Patent
Nicolls et al.

(10) Patent No.: US 9,763,899 B2
(45) Date of Patent: Sep. 19, 2017

(54) IRON CHELATORS AND USE THEREOF FOR REDUCING TRANSPLANT FAILURE DURING REJECTION EPISODES

(71) Applicants: The Board of Trustees of the Leland Stanford Junior University, Stanford, CA (US); The Johns Hopkins University, Baltimore, MD (US); The United States of America as represented by the Department of Veterans Affairs, Washington, DC (US)

(72) Inventors: Mark R. Nicolls, Palo Alto, CA (US); Xinguo Jiang, Palo Alto, CA (US); Geoffrey C. Gurtner, Woodside, CA (US); Gregg L. Semenza, Reisertown, MD (US); Jayakumar Rajadas, Cupertino, CA (US)

(73) Assignees: The Board of Trustees of the Leland Stanford Junior University, Stanford, CA (US); The United States of America as Represented by the Department of Veterans Affairs, Washington, DC (US); The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/653,245

(22) PCT Filed: Dec. 18, 2013

(86) PCT No.: PCT/US2013/076228
§ 371 (c)(1),
(2) Date: Jun. 17, 2015

(87) PCT Pub. No.: WO2014/100233
PCT Pub. Date: Jun. 26, 2014

(65) Prior Publication Data
US 2016/0184244 A1 Jun. 30, 2016

Related U.S. Application Data

(63) Continuation-in-part of application No. PCT/US2013/057544, filed on Aug. 30, 2013.

(60) Provisional application No. 61/739,573, filed on Dec. 19, 2012, provisional application No. 61/695,188, filed on Aug. 30, 2012.

(51) Int. Cl.
| A61K 9/14 | (2006.01) |
| A61K 9/72 | (2006.01) |
| A61K 35/42 | (2015.01) |
| A61K 38/00 | (2006.01) |
| A61K 31/16 | (2006.01) |
| A61K 31/4196 | (2006.01) |
| A61K 31/4412 | (2006.01) |
| A61K 9/00 | (2006.01) |
| A61K 9/12 | (2006.01) |

(52) U.S. Cl.
CPC ............ *A61K 31/16* (2013.01); *A61K 9/0073* (2013.01); *A61K 9/12* (2013.01); *A61K 9/145* (2013.01); *A61K 9/146* (2013.01); *A61K 31/4196* (2013.01); *A61K 31/4412* (2013.01)

(58) Field of Classification Search
None
See application file for complete search history.

(56) References Cited

U.S. PATENT DOCUMENTS

| 4,559,298 A | 12/1985 | Fahy | |
| 6,509,380 B1 * | 1/2003 | Walker, Jr. | ............. A61K 31/16 514/568 |
| 2004/0131703 A1 | 7/2004 | Bach et al. | |
| 2005/0004002 A1 | 1/2005 | Desai et al. | |
| 2010/0316628 A1 | 12/2010 | Breton et al. | |
| 2011/0064794 A1 | 3/2011 | Deng et al. | |

FOREIGN PATENT DOCUMENTS

| WO | 2009/092291 A1 | 7/2009 |
| WO | WO 2014/036414 | 3/2014 |

OTHER PUBLICATIONS

Perrot et al.; Am J Respir Crit Care Med; vol. 167, pp. 490-511 (2003).*
Melillo et al.; JBC, vol. 272, No. 18, Issue of May 2, pp. 12236-12243 (1997).*
Google NPL Search (2 pages); downloaded Aug. 17, 2016.*
SciFinder NPL1 and NPL 2 results; downloaded Aug. 17, 2016.*
Kennedy et al., "Role of Reactive Oxygen Species in Reperfusion Injury of the Rabbit Lung", J Clin Invest. Apr. 1989, pp. 1326-1335, 83(4), The American Society for Clinical Investigation, Inc., Ann Arbor, MI.
Bugaj et al., "The effect of skin permeation enhancers on the formation of porphyrins in mouse skin during topical application of the methyl ester of 5-aminolevulinic acid", Journal of Photochemistry and Photobiology, Jan. 26, 2006, pp. 94-97, Biology 83, Elsevier B.V., Amsterdam, Netherlands.

* cited by examiner

*Primary Examiner* — Jeffrey T Palenik
(74) *Attorney, Agent, or Firm* — Pamela J. Sherwood; Bozicevic, Field & Francis LLP

(57) ABSTRACT

Formulations and methods are provided for improving the function, i.e. clinical outcome, of solid organ transplants. Lung transplantation is of particular interest. In the methods of the invention, a nanoparticle formulation comprising an effective dose of an iron chelator active agent in nanoparticle form, including without limitation, deferoxamine (DFO), deferasirox (DFX), and deferiprone (DFP), etc. is topically applied to the surface of tissues during episodes of graft rejection.

17 Claims, 10 Drawing Sheets

Figure 2A:
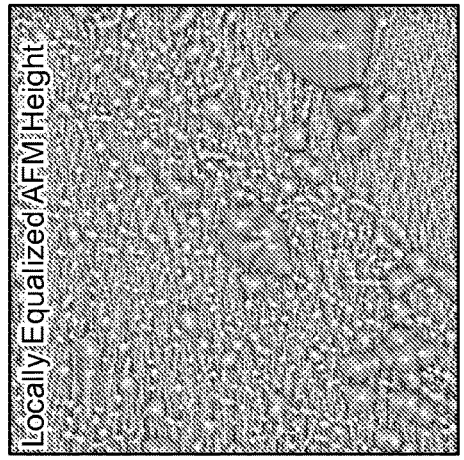

Fig. 1A
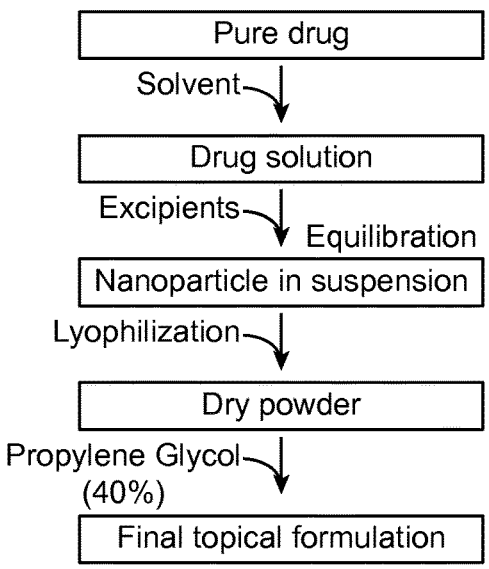
Fig. 1B
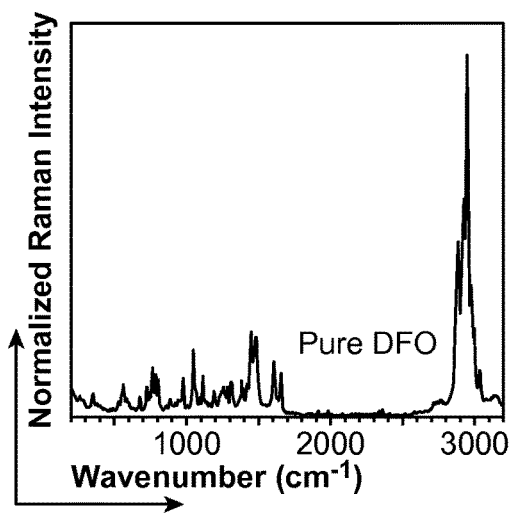
Fig. 1C
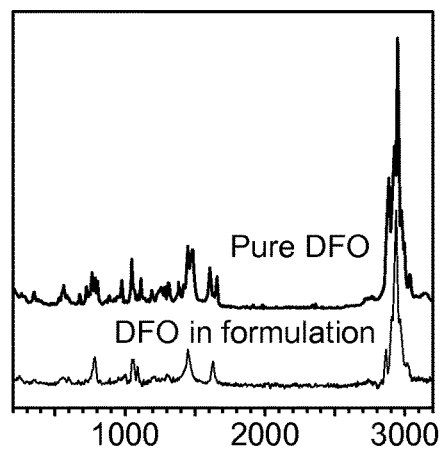
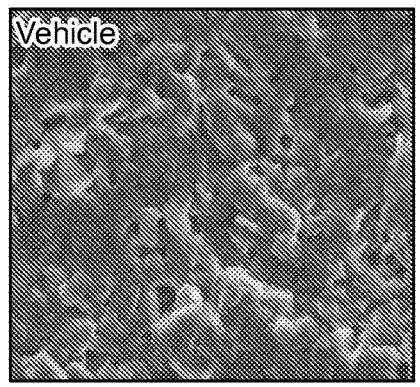
Fig. 1D
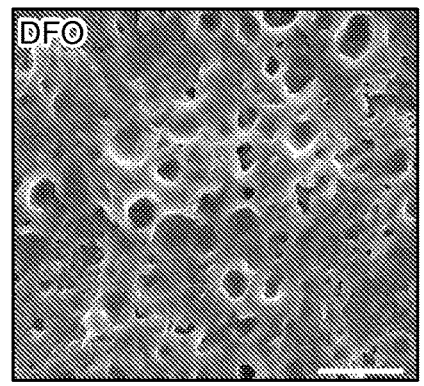
Fig. 1E

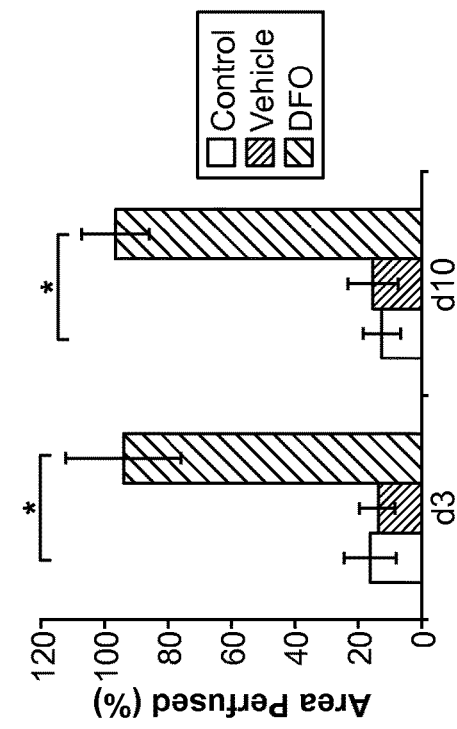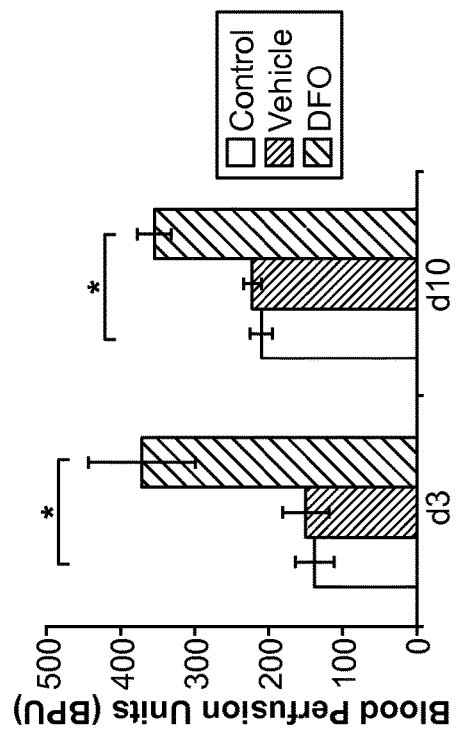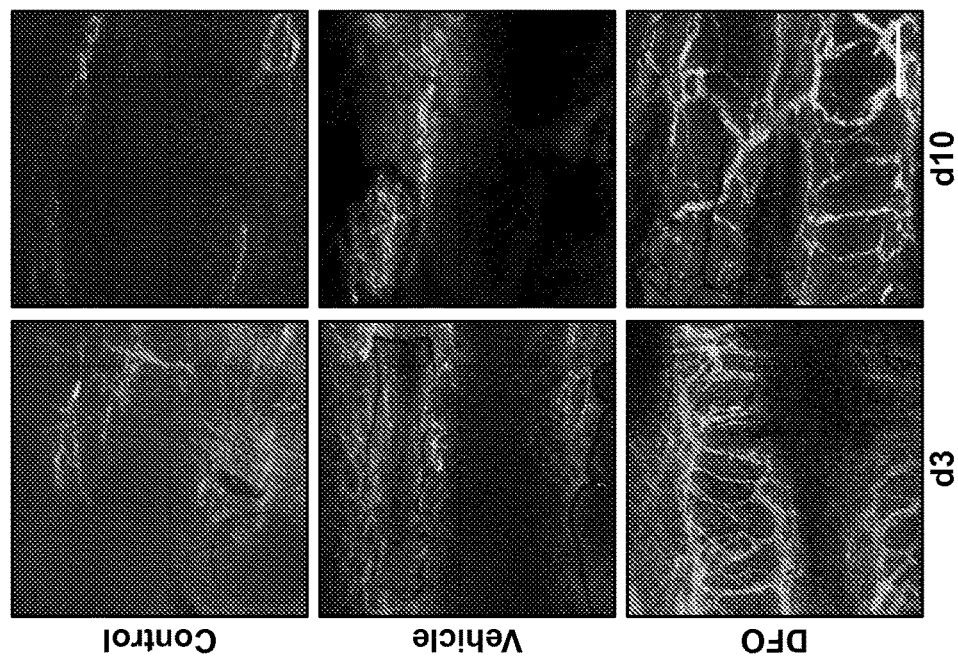

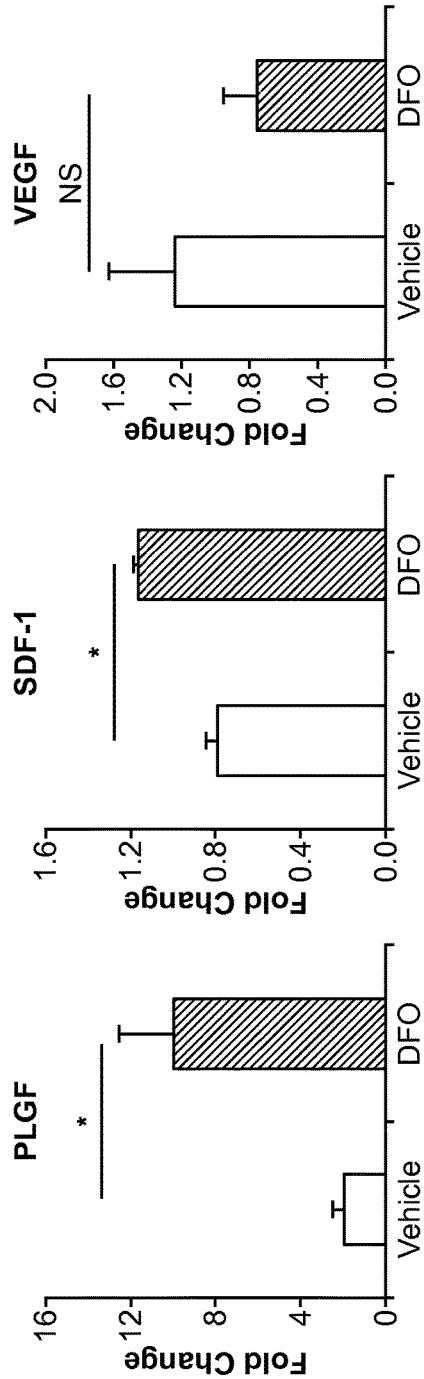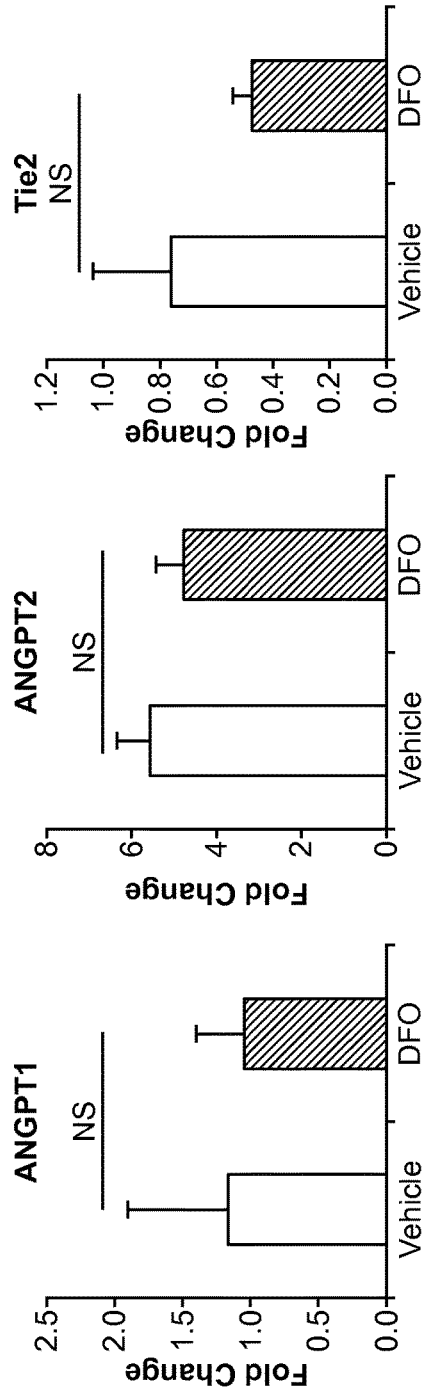

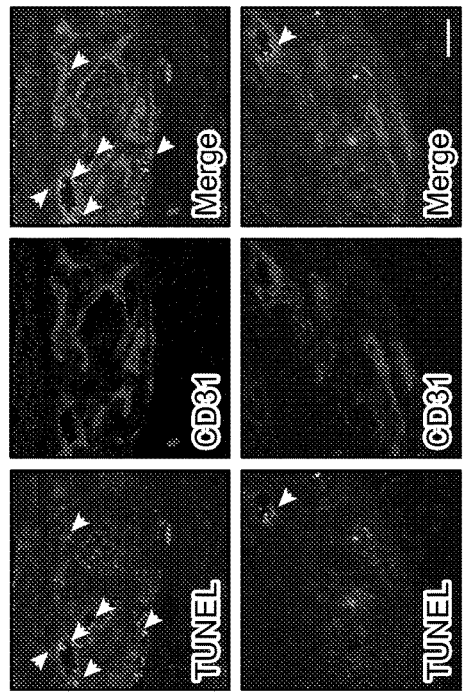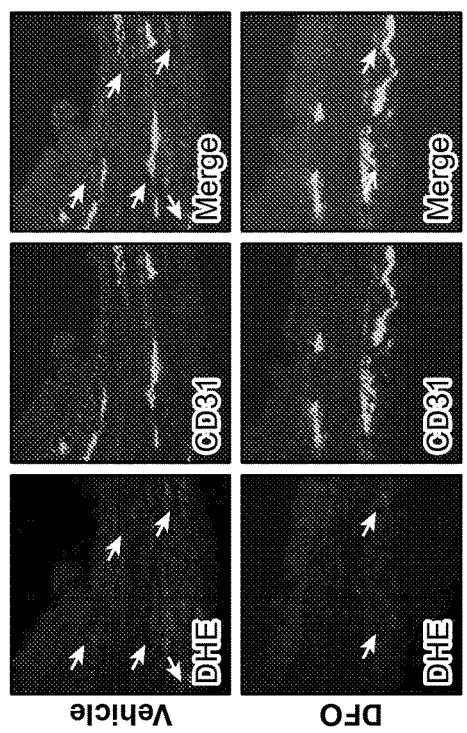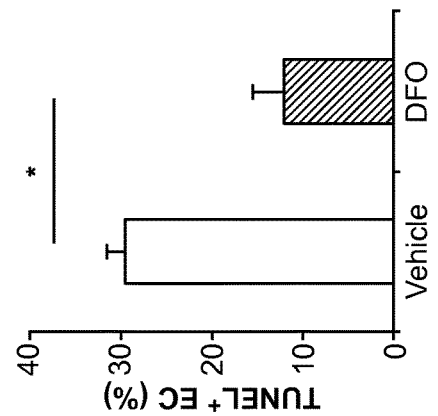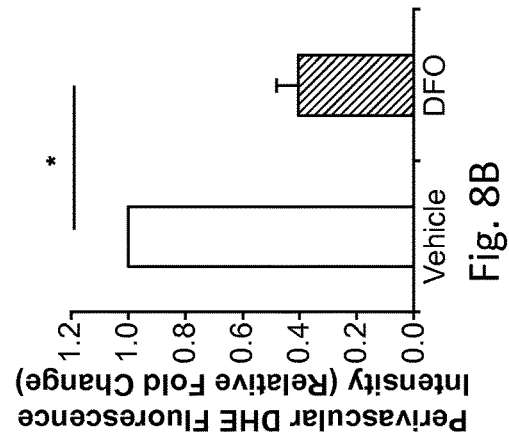
Fig. 8A
Fig. 8C
Fig. 8B
Fig. 8D

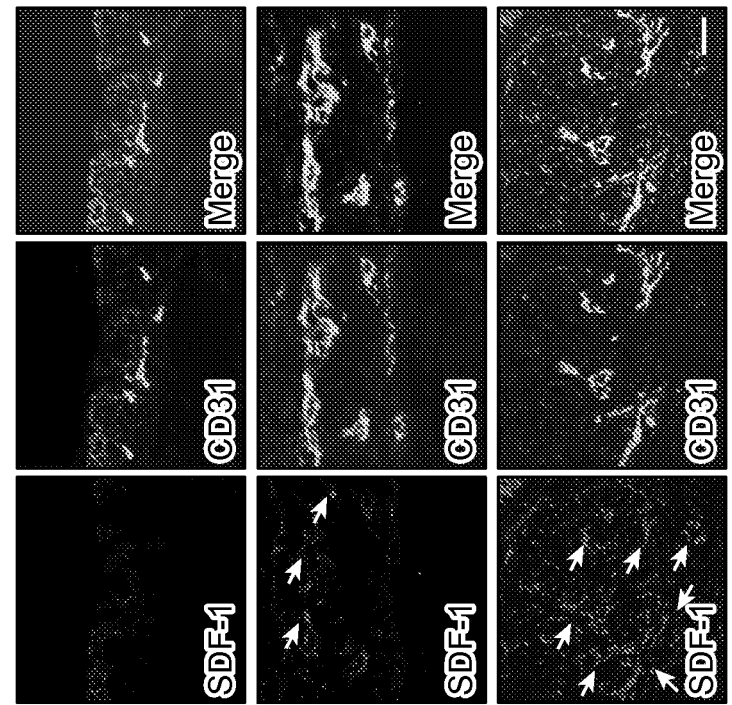
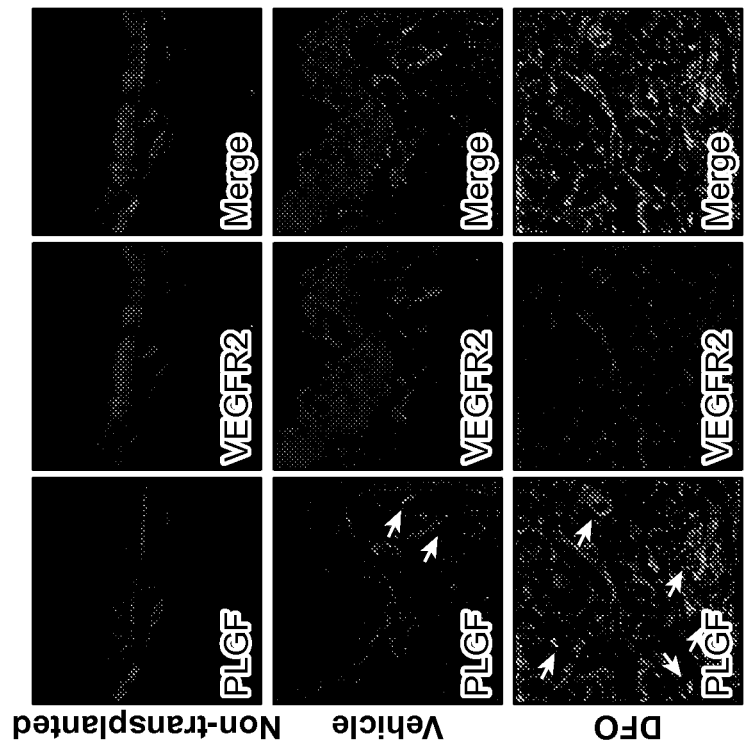

IRON CHELATORS AND USE THEREOF FOR REDUCING TRANSPLANT FAILURE DURING REJECTION EPISODES

This invention was made with Government support under contracts RR025742, HL082662, HL095686, and HL055338, and GM078494, awarded by the National Institutes of Health. The Government has certain rights in this invention.

FIELD OF THE INVENTION

The invention relates to delivery systems of aerosol delivered iron chelators to a transplanted organ or tissue, particularly during rejection episodes.

BACKGROUND

Lung transplantation is the definitive therapy for many end-stage pulmonary diseases and in many cases it is the only therapeutic option, despite having the highest mortality among all solid organ transplants. The fragility and the poor tolerance against ischemia of this organ is responsible for the fact that only 20% of the candidate lungs are currently being transplanted. The success of lung transplantation is limited by acute organ failure as well as chronic rejection against the transplant. Despite the improvement of surgical techniques and the development of better immunosuppressive drugs, short term airway complications taking place at the bronchial anastomosis (where the transplanted airways are surgically connected to the recipient's airways) continue to be a source of morbidity and mortality in those patients. Immediate ischemia of the donor bronchus and sacrifice of bronchial circulation during the surgical procedure have been recognized as the major risk factor for the development of airway complications.

The lung is unique among solid organ transplants in that it is not routinely reattached to the systemic circulation by bronchial arterial revascularization at the time of surgery. Blood supply to the airways in lung transplant recipients is therefore compromised with what blood flow is actually present presumably being provided by the deoxygenated pulmonary artery circulation. Therefore, from the onset, lung transplant airways have an impaired microcirculation due to the lack of a blood supply from the bronchial artery circulation, which results in relative airway tissue hypoxia. It has been previously demonstrated that the lack of bronchial arterial circulation in a lung transplant predisposes the transplanted airway to significant ischemia and hypoxia. It has also been shown that infectious agents can reside in the ischemic area, which includes the bronchial anastomosis of the transplant. Infection is one of the major causes of abnormal healing of the anastomosis as well as increased rate of acute rejection.

Ischemia is the principal factor that stimulates neovascularization, which is primarily regulated by HIF-1; this transcription factor consists of a constitutively expressed HIF-1β subunit and an oxygen-regulated HIF-1α subunit. In the presence of oxygen, two proline residues of HIF-1α are hydroxylated by the prolyl hydroxylase PHD2, facilitating von Hippel-Lindau tumor suppressor gene product (VHL) complex binding and HIF-1α degradation. In hypoxic conditions, PHD2 is inactive and HIF-1α is stabilized. HIF-1α then dimerizes with the β subunit, translocates to the nucleus, and induces gene transcription through binding to hypoxia response elements (HRE) of the oxygen-sensitive genes. HIF-1-mediated transcriptional responses orchestrate the expression of proangiogenic growth factors that facilitate angiogenesis by directly activating resident endothelial cells as well as recruiting circulating angiogenic cells.

Deferoxamine (DFO), deferasirox (DFX), and deferiprone (DFP) are all FDA-approved drugs for the treatment of iron overload conditions. DFO is a bacterial siderophore (N-[5-[[4-[5-[acetyl(hydroxy)amino]pentylamino]-4-oxobutanoyl]-hydroxyamino] pentyl]-N'-(5-aminopentyl)-N'-hydroxybutanediamide), DFX is a synthetic oral iron chelator (4-[(3Z,5E)-3,5-bis(6-oxocyclohexa-2,4-dien-1-ylidene)-1,2,4-triazolidin-1-yl]benzoic acid), DFP is an oral iron chelator (1,2-dimethyl-3-hydroxypyrid-4-one).

DFO, DFX and DFP have been extensively studied in various disease models. DFO can induce the transcriptional activity of HIF-1α in tumors. DFO stabilizes HIF-1α from degradation by inhibiting the activity of the PHDs through depletion of $Fe^{2+}$. Both DFO and DFX were shown to promote β cell function through upregulation of HIF-1α. In a rat median nerve injury model, local administration of DFO-loaded lipid particle promoted end-to-end nerve reconstruction. Through stabilizing HIF-1α protein, DFO has recently been shown to potentiate the homing of mesenchymal stem cells to promote target tissue regeneration. In a mouse hind limb ischemia model, DFO was shown to promote vascular repair and relief tissue ischemia.

Drug-loaded nanoparticles have emerged as a promising strategy for efficient drug delivery for the treatment of a variety of diseases. Drugs encapsulated in nanoparticles may display increased availability due to higher specific surface area and biocompatibility of the formulated particles.

As the size of a particle decreases, the surface area to the volume ratio increases, leading to an increased dissolution velocity, as described by Noyes-Whitney equation. Additionally, the saturation solubility of a particle increases as the particle size decreases, as described by the Kelvin and Ostwald-Freundlich equation, particularly after the particle size falls below about 1 μm. These phenomena make a nanoparticle formulation a highly effective means to enhance mass transfer from the particle to the surrounding medium. By suspending a drug as nanoparticles, one can achieve a dose that is higher than that of a solution, which is thermodynamically limited by the aqueous solubility of drug.

The loss of microvascular circulation after lung transplantation may occur, and lead to episodes of chronic organ rejection. Therefore, preserving the architectural integrity of the microvascular circulation is an important consideration for preventing chronic rejection. Increased levels of hypoxia inducible factor (HIF) in the donor airway promote its angiogenesis and diminishes ischemia and hypoxia following transplantation. Increasing HIF levels in the transplanted human airway by local administration of a HIF1a potentiating agent may promote angiogenesis during rejection episodes. The present invention addresses this issue.

SUMMARY

Formulations and methods are provided for improving the function, i.e. clinical outcome, of a lung transplant. By providing formulations that increase neovascularization at a critical site and location, for example during acute rejection episodes, particularly with respect to lung transplantation, improved blood perfusion and graft health is provided. The present invention provides formulations for administration of a HIF-1α stabilizer in a nanoparticle formulation. In some embodiments the nanoparticle formulation is administered as an aerosol, particularly in the treatment of acute rejection episodes of a transplanted lung, where the formulation provides a dose that is effective in increasing neovascularization of the graft.

In one embodiment, a HIF-1α stabilizer is an iron chelator such as, deferoxamine (DFO), deferasirox (DFX), and deferiprone (DFP). In other embodiments, the iron chelator is selected from the group consisting of PIH (pyridoxal isonicotinoyl hydrozone), DFT (a desferrithiocin), DBED (N,N'-bis-dibenzyl ethylenediaminediacetic acid), FDO (a furildioxime), BDP (dexrazoxane), ZIL (Zileuton), DOX (doxorubicin), BHT (a bis-hydroxylaminetriazine), HBP (a 3-hydroxybezopyran-4-one), CAC (enterobactin), Triapine and ciclopirox, Lactoferrin, DP44mT, clioquinol, sideromycines, Salicylaldehyde isonicotinoyl hydrazine, S956711, FG-0041, TM6008, and analogs of any of the foregoing with iron chelating activity.

In another embodiment, HIF-1α stabilizer is a non-iron-chelating PHD inhibitor. In various embodiments, the PHD inhibitor is selected from a group consisting of TM6089, FG-4592, FG-2216, JNJ42041935, FG-4497, EDHB (ethyl-3,4-dihydroxybenzoate), DMOG (dimethyloxallyl glycine), N-OG (N-oxalyglycine), DHB (3,4-dihydroxybenzoate), IOX2 (Axon1921), IOX1, Axon1948, 2,4-DPD, GSK360A, FG-6515, 1,4-DPCA (4,4α-dihydro-4-oxo-1,10-phenanthroline-3-carboxylic acid), ICA ((PHD-I) 2-(1-chloro-4-hydroxyisoquinoline-3-carboxamido) acetate), and analogs of any of the forgoing with non-iron-chelating PHD inhibiting activity.

In preferred embodiments the HIF-1α stabilizer is formulated as encapsulated nanoparticles. A nanoparticle formulation provides the advantages of delivery over an extended period of time; and targeted to the interior of cells to stabilize HIF-1α. Encapsulation improves the sustained release.

The formulation of the invention comprises an effective dose of a HIF-1α stabilizer in a nanoparticle form, where the active agent may be at least about 5% of the total nanoparticle weight, and not more than about 50% of the total nanoparticle weight. The nanoparticle formulation of the HIF-1α stabilizer may be provided in a suitable composition for aerosol administration. For example, the stabilizer may be an aqueous solution of drug, i.e., drug dissolved in water and formed into small particles to create an aerosol that is delivered to the patient. Alternatively, liquid suspensions or dry powders, which are intermixed with an airflow in order to provide for delivery of drug to the patient may be used. Alternatively, the drug may be in a solution wherein a low-boiling point propellant is used as a solvent.

In other embodiments of the invention, the aerosol formulation is delivered to a patient suffering from an acute rejection episode of a lung graft, the method comprising a pulmonary administration of an aerosol formulation of the invention. The dose delivered is effective in improving the microvasculature of the graft, i.e. blood flow to the engrafted tissue is improved relative to the condition of the tissue in the absence of the treatment.

An effective dose of active agent is that dose which, when provided to a patient, is effective in improving microvascular perfusion at the transplanted organ, for example in improving airway microvascular perfusion after a period of from about 3 to about 10 days, relative to a control transplant in the absence of treatment with the methods of the invention. An effective dose may vary depending on the active agent and the size of the surface that is being treated. In some embodiments, e.g. using DFO as an active agent, the effective dose for administration at the time of a rejection episode may be at least about 10 mg, at least about 50 mg, and not more than about 1000 mg, usually not more than about 500 mg, or not more than about 200 mg, and may be from about 100 mg to about 500 mg.

The nanoparticles are usually comprised of the active agent and a pharmaceutically acceptable stabilizer, where the active agent may be at least about 5% of the total nanoparticle weight, and not more than about 50% of the total nanoparticle weight. The nanoparticles may be suspended in a pharmaceutically acceptable carrier at a concentration that provides for the desired dose of active agent.

The composition may be packaged for use during surgery, in a sterile unit dose, optionally with applicator, and may include labeling and/or instructions for use.

BRIEF DESCRIPTION OF THE DRAWINGS

FIG. 1A-1E. Analysis of drug molecule structure and morphology study of encapsulated nanoparticles. FIG. 1A. A schematic showing the procedure for nanoparticle formulation. FIG. 1B and FIG. 1C. Drug structure analysis by Raman spectroscopy showing the structures of pure DFO (FIG. 1B) and DFO in the nanoparticle formulation (FIG. 1C). FIG. 1D and FIG. 1E. Nanoparticle morphology analysis shows that the vehicle (FIG. 1D) and DFO dry powders (FIG. 1E) are homogeneous. Scale bar: 20 μm (FIG. 1D, FIG. 1E).

FIG. 2A-2F. Sample homogeneity analysis of DFO in nanoparticle islands on a Si wafer. FIG. 2A-2F. DFO sample homogeneity was assessed by optical image (FIG. 2A), AFM height (FIG. 2B), locally equalized AFM height (FIG. 2C), AFM phase shift (FIG. 2D), confocal Raman maps of DFO (red arrows) (FIG. 2E) and the excipient (green arrows) (FIG. 2F). The Raman confocal maps were acquired by integrating the intensities of the following peaks: DFO peak centered at 1620 $cm^{-1}$ (1600-1640 $cm^{-1}$) (FIG. 2E) and excipient peak at 1655-1695 $cm^{-1}$ (FIG. 2F). Scale bar: 5 μm.

FIG. 3A-3C. Assessment of the nanoparticle penetration into tracheas. FIG. 3A. Kinetics of DFO nanoparticle penetration into mouse tracheas. FIG. 3B and FIG. 3C. Analysis of the depth of the nanoparticle penetration into pig (FIG. 3C) and human tracheas. The DFO concentrations were measured by HPLC (FIG. 3A to FIG. 3C). Data are shown as means±SEM.

FIG. 4A-4C. Subepithelial cellular localization of nanoparticle formulations. FIG. 4A and FIG. 4B. Confocal microscopy images showing the subepithelial cellular distribution of vehicle alone nanoparticles (FIG. 4A) and DFO nanoparticles (FIG. 4B). FIG. 4C. Quantification of cellular nanoparticle localization by percentage of cells with cytoplasmic fluorescence. Red: Rhodamine-labeled DSPE-PEG identifies the lipid vehicles of the nanoparticles; Blue: Nuclear staining by DAPI. White arrows: cells with no cytoplasmic fluorescent signal. Data are shown as means±SEM. NS, not significant, Student's t test (FIG. 4C). Scale Bar: 20 μm (FIG. 4A, FIG. 4B).

FIG. 5A-5C. Effects of DFO nanoparticle formulation on airway microvascular perfusion. FIG. 5A. Confocal microscopic imaging showing microvascular perfusion of non-, vehicle- and DFO nanoparticle-treated airway allografts at d3 and d10 following transplantation. FIG. 5B. Quantification of perfused airway microvasculature following transplantation. FIG. 5C. Airway blood perfusion measured by laser Doppler flowmetry at d3 and d10 following transplantation. Scale bar: 100 μm (FIG. 5A). Data are shown as means±SEM. *$P<0.05$, Student's t test (FIG. 5B, FIG. 5C).

FIG. 6A-F. Analysis of angiogenic growth factors and associated angiogenic cytokines. FIG. 6A-6E. Real time RT-PCR analysis of mRNA expression of angiogenic growth factors in d3 airway allografts treated with vehicle or DFO nanoparticles (n=3-5). FIG. 6F. Real time RT-PCR analysis of Tie2 mRNA expression in d3 allografts treated with vehicle or DFO nanoparticles (n=3-5). Data are shown as means±SEM. NS, not significant; *P<0.05, Student's t test.

Figure 7A:
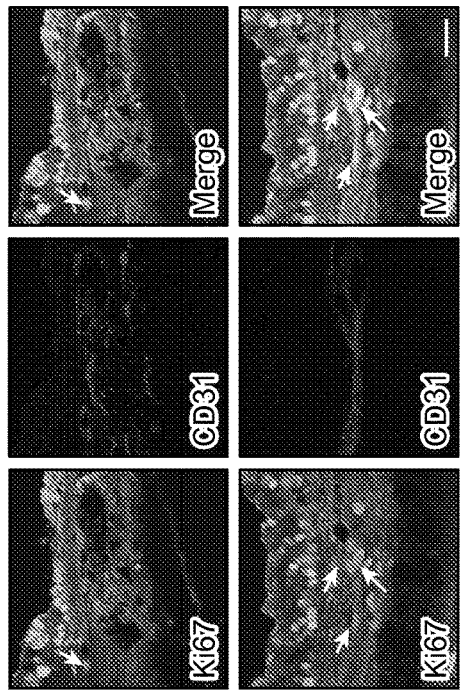
Figure 7C:
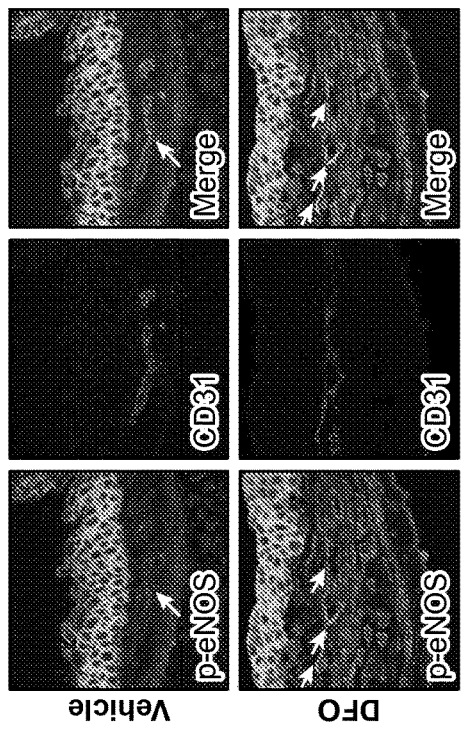
Figure 7B:
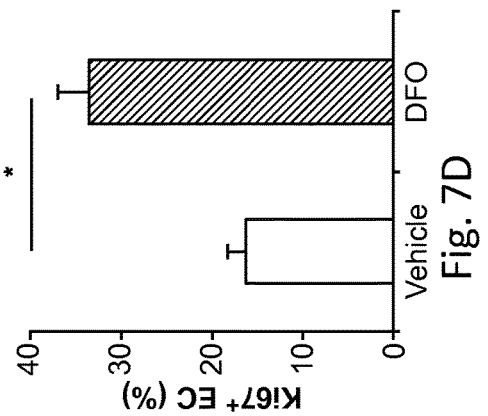
Figure 7D:
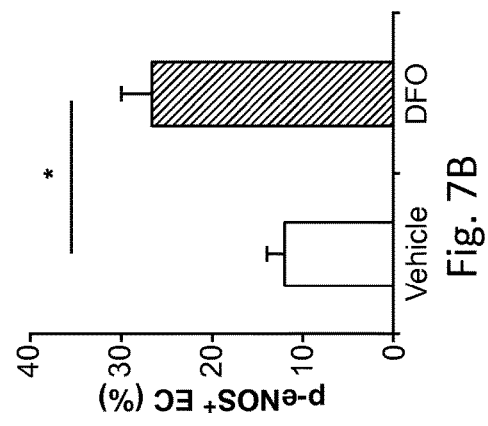

FIG. 7A-7D. Increased levels of p-eNOS and Ki67 in the endothelial cells of tracheas treated with DFO nanoparticles. FIG. 7A, FIG. 7C. Confocal microscopic images showing increased p-eNOS (green, white arrows) and Ki67 (green, white arrows) in ECs of DFO treated airways. FIG. 7B, FIG. 7D. Quantification of p-eNOS$^+$ cells and Ki67$^+$ cells (n=3-5). Scale bars: 20 μm (FIG. 7A, FIG. 7C). Data are shown as means±SEM. *P<0.05, Student's t test (FIG. 7B, FIG. 7D).

FIG. 8A-8D. Decreased levels of perivascular ROS production and endothelial cell apoptosis in DFO treated tracheas. FIG. 8A, FIG. 8C. Confocal microscopic images showing decreased perivascular ROS production by DHE staining (red, white arrows) and EC apoptosis by TUNEL staining (green, white arrows). FIG. 8B, FIG. 8D. Quantification of perivascular DHE staining and EC TUNEL staining (n=3-5). Scale bars: 20 μm (FIG. 8A, FIG. 8C). Data are shown as means±SEM. *P<0.05, Student's t test (FIG. 8B, FIG. 8D).

Figure 9A:
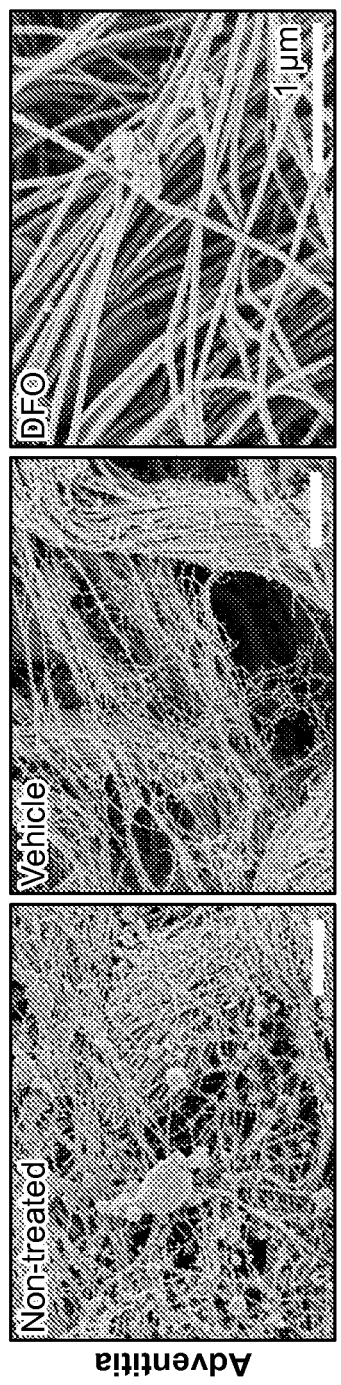
Figure 9B:
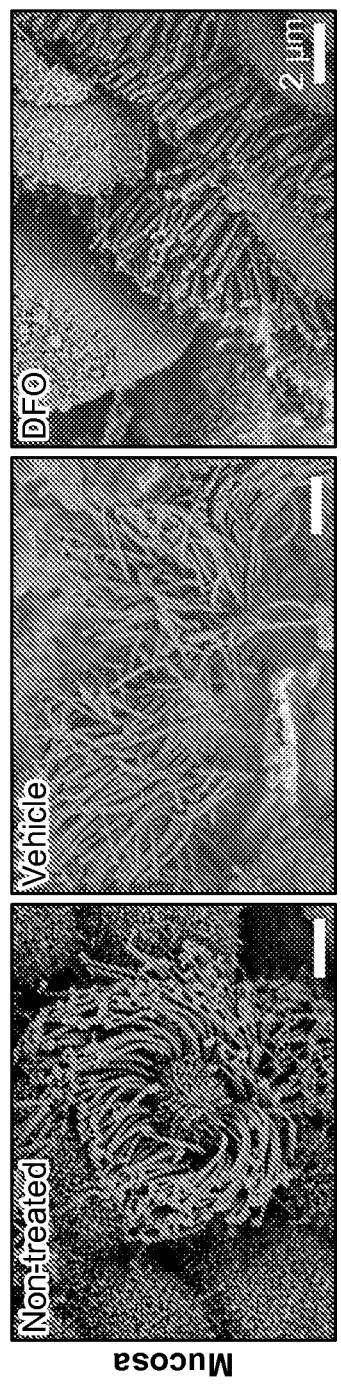

FIG. 9A-9B. SEM images of mouse tracheas following incubation in vehicle or nanoparticle solution. Tracheas were examined by SEM following a 10 min incubation in the nanoparticle solution. FIG. 9A, FIG. 9B. Adventitial layer (FIG. 9A) and mucosal layer (FIG. 9B) of non-, vehicle-, and nanoparticle-treated tracheas.

FIG. 10A-10B. Immunofluorescent staining of PLGF and SDF-1 in vehicle- or DFO-treated d3 airway allografts. FIG. 10A, FIG. 10B. Augmented PLGF staining (green, white arrows) (FIG. 10A) and SDF-1 staining (red, white arrows) (FIG. 10B) were observed in DFO-treated d3 allografts. VEGFR2 (FIG. 10A) and CD31 (FIG. 10B) were used to as endothelial cell markers. Scale bar: 20 μm.

DETAILED DESCRIPTION OF THE EMBODIMENTS

The clinical outcome of a solid organ transplantation, including without limitation lung transplantation, during a rejection episode is improved by aerosol administration of an iron chelator active agent in nanoparticle form, including without limitation, deferoxamine (DFO), deferasirox (DFX), and deferiprone (DFP), etc. Targeting the neovascularization cascade reverses the impairments seen with chronic rejection episodes.

Before the present methods are described, it is to be understood that this invention is not limited to particular methods described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges encompassed within the invention, subject to any specifically excluded limit in the stated range.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a microsphere" includes a plurality of such microspheres and reference to "the stent" includes reference to one or more stents and equivalents thereof known to those skilled in the art, and so forth.

Definitions

The terms "treating", and "treatment" and the like are used herein to generally mean obtaining a desired pharmacological and/or physiological effect. The effect may be prophylactic in terms of preventing or partially preventing a disease, symptom or condition thereof and/or may be therapeutic in terms of a partial or complete cure of a condition, symptom or adverse effect attributed to the condition. The term "treatment" as used herein covers particularly the topical application of a composition comprising an iron chelator active agent in nanoparticle form at the site of trachea anastomosis. The term "prophylaxis" is used herein to refer to a measure or measures taken for the prevention or partial prevention of a disease or condition.

The term "subject" includes mammals, e.g. cats, dogs, horses, pigs, cows, sheep, rodents, rabbits, squirrels, bears, primates such as chimpanzees, gorillas, and humans.

As used herein, the term "solid organ transplantation" is used in accordance with the conventional meaning of the term, where an organ from a donor, which donor may be living or deceased, in placed into the body of a recipient in the appropriate position and cardiovascular connections to be physiologically integrated into the recipient. Transplantation of lung(s) is of particular interest for the methods of the invention, although the methods do not exclude transplantation of other organs, e.g. pancreas and including kidney, pancreatic islet cells; heart; intestine, liver; skin, and the like as known in the art. In some embodiments the transplantation involves multiple anastomoses, e.g. transplantation of lung, heart, liver, kidney. The transplanted organ may be referenced as a "graft", and the physiological integration of the organ may be referred to as engraftment.

The term "graft management" refers to therapeutic methods that induce and/or promote repair engraftment of a solid organ, but not limited to, lung transplantation.

As used herein, the term "iron chelating compound" or "iron chelator" is intended to mean a compound that binds iron between one or more binding sites so as to form a chelate. An iron chelating compound bound or complexed with iron is referred to herein as an iron chelator. Chelators may be categorized by their binding structures. Deferiprone (DFP) is a bidentate chelator requiring three molecules each with two iron binding sites for the six coordination sites of iron(III). Deferasirox (DFX), a tridentate chelator, requires two molecules for iron(III) coordination, and desferrioxamine (DFO) is a hexadentate chelator binding iron in a 1:1 ratio.

Iron chelating compounds useful in the methods and formulations of the invention include chelation compounds that can bind to all oxidation states of iron including, for example, iron (-II) state, iron (-I) state, iron (0) state, iron (I) state, iron (II) state (ferrous), iron (III) state (ferric), iron (IV) state (ferryl) and/or iron (V). Iron chelation therapy refers to the use of an iron chelator to bind with iron in vivo to form an iron chelate so that the iron loses its toxic effect or adverse physiological activity.

An iron chelating compound useful in a composition of the invention can include any chelator or other molecule that can bind and prevent iron utilization. Specific examples of iron chelating compounds included in the compositions of the invention include, for example, deferoxamine, deferiprone and deferasirox. These exemplary iron chelating compounds are particularly useful because they have been approved in various countries for therapeutic indications and are therefore, well characterized, safe and non-toxic in humans.

The term "deferoxamine" (also known as desferrioxamine B, desferoxamine B, DFO-B, DFOA, DFB, DFO or desferal) is a bacterial siderophore produced by the actinobacteria *Streptomyces pilosus*, having the structure (N-[5-[[4-[5-[acetyl(hydroxy)amino]pentylamino]-4-oxobutanoyl]hydroxyamino] pentyl]N'-(5-aminopentyl)-N'-hydroxybutanediamide). It has medical applications including, for example, as a chelating agent to remove excess iron from the body. The mesylate salt of DFO-B is commercially available.

The term "deferiprone," as it is used herein is intended to mean an iron chelating compound having the structure 1,2 dimethyl-3-hydroxypyrid-4-1. Deferiprone (DFP), also is known in the art as L1, CP20, Ferriprox, or Kelfer. Deferiprone, is a member of the α-ketohydroxypyridine class of iron chelators and is commercially available from, for example, Apotex, Inc. (Weston, Ontario, Canada).

The term "deferasirox" as it is used herein is intended to mean an iron chelating compound having the structure 4-[3,5-Bis(2-hydroxyphenyl)-1H-1,2,4-triazol-1-yl]benzoic acid and having a molecular weight of 373.4 daltons. Deferasirox, also is known in the art as DFX, Exjade® or ICL 670, is a member of the class of tridentate iron chelators referred to as N-substituted bis-hydroxyphenyl-triazoles. Deferasirox is commercially available from, for example, Novartis, Corp. (Basel, Switzerland), for example, under the trademark Exjade®. According to the present invention, the terms "deferasirox", "ICL670", "Exjade®" are meant to refer to the active ingredient 4-[3,5-Bis(2-hydroxyphenyl)-1H-1,2,4-triazol-1-yl]-benzoic acid, e.g. 4-[3,5-Bis(2-hydroxyphenyl)-1H-1,2,4-triazol-1-yl]benzoic acid or a pharmaceutically acceptable salt thereof. Deferasirox, its process of manufacture and its uses are described in, for example, U.S. Pat. Nos. 6,465,504B1 and 6,595,750 B2, and in European Patent No. EP0914118. Pharmaceutical preparations comprising 4-[3,5-Bis(2-hydroxyphenyl)-1H-1,2,4-triazol-1-yl]benzoic acid or a pharmaceutically acceptable salt thereof are described in, for example, International Patent Application WO2004/035026.

Other iron chelating compounds also can be included in the compositions of the invention. Such other iron chelating compounds are well known in the art and include, for example, naturally occurring siderophores and xenosiderophores as well and non-naturally occurring compounds such as deferiprone and deferasirox.

Non-naturally occurring iron chelating compounds are exemplified by members of the hydroxypyridin-4-one (HPO) class of chelators, such as deferiprone, members of the N-substituted bis-hydroxyphenyl-triazole class of chelators such as deferasirox, diethylenetriaminepentaacetic acid (DTPA) and deferoxamine. Deferiprone, deferasirox and any of the above exemplary iron chelating compounds as well as others well known in the art can be included in the iron chelating compound containing compositions of the invention.

Siderophores and xenosiderophores include, for example, hydroxamates and polycarboxylates. The hydroxamates contain an N-δ-hydroxyornithine moiety and are generally categorized into four exemplary families. One category includes rhodotorulic acid, which is the diketopiperazine of N-δ-acetyl-L-N δ-hydroxyornithine. Included within this category are derivatives such as dihydroxamate named dimerum acid. A second category includes the coprogens, which contain an N-δ-acyl-N-δ-hydroxy-L-ornithine moiety. Coprogens also can be considered trihydroxamate derivatives of rhodotorulic acid with a linear structure. A third category includes the ferrichromes, which consist of cyclic peptides containing a tripeptide of N-δ-acyl-N-δ-hydroxyornithine and combinations of glycine, serine or alanine. The fourth exemplary category includes the fusarinines, also called fusigens, which can be either linear or cyclic hydroxamates. Fusarinine is a compound characterized by N acylation of N-hydroxyornithine by an hydromevalonic acid.

The polycarboxylates consist of a citric acid-containing polycarboxylate called rhizoferrin. The molecule contains two citric acid units linked to diaminobutane. Rhizoferrin is widely distributed among the members of the phylum Zygomycota, having been observed in the order Mucorales and in the order Entomophthorales. Other categories of siderophores useful as iron chelating compounds in the compositions of the invention include, for example, the phenolate-catecholate class of siderophores, hernin, and β-ketoaldehyde phytotoxins.

The amount of iron chelating compound included in a composition of the invention can vary but will generally be a therapeutically effective amount or an amount that can be reconstituted or diluted to a therapeutically effective amount. For example, effective amounts of iron chelating compounds of the invention are described further below with reference to the methods of the invention. An amount of one, some or all iron chelating compounds can be formulated in a composition of the invention to correspond to these exemplary effective amounts.

An iron chelating compound also can be formulated in a composition of the invention in amounts greater than a therapeutically effective amount for either short or long-term storage and the end user can dilute the formulation prior to use to a desired therapeutically effective amount. Alternatively, an iron chelating compound included in a composition of the invention can be lyophilized or produced in powder or other solid form and the end user can reconstitute the dry formulation prior to use to a desired therapeutically effective amount.

In some embodiments, the iron chelating agent is a HIF-1α potentiating agent, or alternatively a HIF-1α potentiating agent other than an iron chelator. HIF-1 is an oxygen-dependent transcriptional activator, which plays crucial roles in the angiogenesis of tumors and mammalian development. HIF-1 consists of a constitutively expressed HIF-1β subunit and one of three subunits (HIF-1α, HIF-2α or HIF-3α). The stability and activity of HIF-1α are regulated by various post-translational modifications, hydroxylation, acetylation, and phosphorylation. Under normoxia, the HIF-1α subunit is rapidly degraded via the vHL-mediated ubiquitin-proteasome pathway. The association of vHL and HIF-1α under normoxic conditions is triggered by the hydroxylation of prolines and the acetylation of lysine within a polypeptide segment known as the oxygen-dependent degradation (ODD) domain. During hypoxic conditions HIF-1α subunit becomes stable and interacts with coactivators such as p300/CBP to modulate its transcriptional activity.

HIF-1 acts as a master regulator of numerous hypoxia-inducible genes under hypoxic conditions. The heterodimer HIF-1 binds to the hypoxic response elements (HREs) of target gene regulatory sequences, resulting in the transcription of genes implicated in the control of cell proliferation/survival, glucose/iron metabolism and angiogenesis, as well as apoptosis and cellular stress. Some of these direct target genes include glucose transporters, the glycolytic enzymes, erythropoietin, and angiogenic factor vascular endothelial growth factor (VEGF).

The term "HIF-1", as used herein, includes both the heterodimer complex and the subunits thereof, HIF-1α and HIF-1. The HIF 1 heterodimer consists of two helix-loop-helix proteins; these are termed HIF-1α, which is the oxygen-responsive component (see, e.g., Genbank accession no. Q16665), and HIF-1β. The latter is also known as the aryl hydrocarbon receptor nuclear translocator (ARNT).

HIF-1α potentiating agents include agents that increase the accumulation of, or stability of, HIF-1α; directly provide HIF-1α activity; or increase expression of HIF-1. Such agents are known in the art, or may be identified through art-recognized screening methods.

Compounds currently identified as HIF-1 potentiating agents include cofactor-based inhibitors such as 2-oxoglutarate analogues, ascorbic acid analogues and iron chelators such as desferrioxamine (DFO), the hypoxia mimetic cobalt chloride ($CoCl_2$), and mimosine, 3-Hydroxy-4-oxo-1(4H)-pyridinealanine, or other factors that may mimic hypoxia. Also of interest are hydroxylase inhibitors, including deferiprone, 2,2'-dipyridyl, ciclopirox, dimethyloxallyl glycine (DMOG), L-Mimosine (Mim) and 3-Hydroxy-1,2-dimethyl-4(1H)-Pyridone (OH-pyridone). Other HIF hydroxylase inhibitors are described herein, including but not limited to, oxoglutarates, heterocyclic carboxamides, phenanthrolines, hydroxamates, and heterocyclic carbonyl glycines (including, but not limited to, pyridine carboxamides, quinoline carboxamides, isoquinoline carboxamides, cinnoline carboxamides, beta-carboline carboxamides, including substituted quinoline-2-carboxamides and esters thereof; substituted isoquinoline-3-carboxamides and N-substituted arylsulfonylamino hydroxamic acids (see, e.g., PCT Application No. WO 05/007192, WO 03/049686 and WO 03/053997), and the like.

Compounds reported to stabilize HIF-1α also include [(3-hydroxy-6-isopropoxy-quinoline-2-carbonyl)-amino]-acetic acid, [3-hydroxy-pyridine-2-carbonyl)-amino]-acetic acid, [N-((1-chloro-4-hydroxy-isoquinoline-3-carbonyl)-amino)-acetic acid, [(7-bromo-4-hydroxy-isoquinoline-3-carbonyl)-amino]-acetic acid, [(7-chloro-3-hydroxy-quinoline-2-carbonyl)-amino]-acetic acid, [(1-bromo-4-hydroxy-7-kifluoromethyl-isoquinoline-3-carbonyl)-amino]-acetic acid, [(1-Bromo-4-hydroxy-7-phenoxy-isoquinoline-3-carbonyl)-amino]-acetic acid, [(1-Chloro-4-hydroxy-7-phenoxy-isoquinoline-3-carbonyl)-amino]-acetic acid, [(1-Chloro-4-hydroxy-7-methoxy-isoquinoline-3-carbonyl)-amino]-acetic acid, [(1-chloro-4-hydroxy-isoquinoline-3-carbonyl)-amino]-acetic acid, [(4-Hydroxy-7-phenoxy-isoquinoline-3-carbonyl)-amino]-acetic acid, [(4-Hydroxy-7-phenylsulfanyl isoquinoline-3-carbonyl)-amino]-acetic acid, [(4-Hydroxy-6-phenylsulfanyl-isoquinoline-3-carbonyl)-amino]-acetic acid, 4-Oxo-1,4-dihydro-[1,10]phenanthroline-3-carboxylic acid, 4-hydroxy-5-methoxy-[1,10] phenanthroline-3-carboxylic acid ethyl ester, [(7-benzyloxy-1-chloro-4-hydroxy-isoquinoline-3-carbonyl)-amino]-acetic acid methyl ester, and 3-{[4-(3,3-Dibenzyl-ureido)-benzenesulfonyl]-[2-(4-methoxy-phenyl)-ethyl]-amino}-N-hydroxy-propionamide.

The term "pharmaceutically acceptable" as used herein refers to a compound or combination of compounds that will not impair the physiology of the recipient human or animal to the extent that the viability of the recipient is compromised. Preferably, the administered compound or combination of compounds will elicit, at most, a temporary detrimental effect on the health of the recipient human or animal.

The formulations of the invention can comprise nanoparticles of an iron chelating active agent, or a non-chelating HIF-1α stabilizing agent as described above, and generally admixed with a stabilizer or cocktail of stabilizers. The nanoparticle can comprise or consist essentially of the active agent at a concentration of up to about 5%, up to about 10%, up to about 15%, up to about 20%, up to about 25%, up to about 30%, up to about 35%, up to about 40%, up to about 45%, up to about 50%, up to about 55%, up to about 60%, up to about 65%, up to about 70%, up to about 75% of the total weight, and the like. It will be understood by one of skill in the art that two or more active compounds can be co-formulated, in which case the purity shall refer to the combined active agents.

In some embodiments the nanoparticle comprises from about 40% to about 60% by weight active agent, and may comprise from about 45% to about 50% by weight active agent.

The balance of the nanoparticle weight is provided by stabilizer, i.e. up to about 95%, up to about 90%, up to about 85%, up to about 80%, up to about 75%, up to about 70%, up to about 65%, up to about 60%, up to about 55%, up to about 50%, up to about 45%, up to about 40% of the total weight.

In some embodiments the nanoparticle comprises from about 40% to about 60% by weight stabilizer, and may comprise from about 50% to about 55% by weight stabilizer or combination of stabilizers.

The nanoparticles have a controlled size, as appropriate for optimization of drug delivery. Usually the particle will have a diameter of up to about 10 nm, up to about 50 nm, up to about 100 nm, up to about 250 nm, up to about 500 nm, up to about 1 μm, up to about 2.5 μm, up to about 5 μm, and not more than about 10 μm in diameter. In some embodiments the nanoparticle size is from about 100 nm to about 5 μm in diameter, for example from about 100 nm to about 500 nm, from about 500 nm to about 1 μm, and the like. The nanoparticle optionally has a defined size range, which may be substantially homogeneous, where the variability may not be more than 100%, 50%, or 10% of the diameter.

Nanoparticles can be formed by various methods, including, in some embodiments, the methods exemplified herein. Methods of interest may include, without limitation, particles precipitated out of solution (bottom-up) for example by lyophilization, or milled from larger particles (top-down). In both mechanisms, the total surface area increases which increases the free energy of the particles. The system compensates for this increase in free energy by dissolving crystalline nuclei and precipitating onto other particles in a process known as Ostwald Ripening or by agglomerating smaller particles. Some processes that are currently under investigation include: wet milling, supercritical fluid extraction, spray drying; electro-spray; high-pressure homogenization; and recrystallization via solvent displacement. In addition to chemical processing technologies, multiple studies have examined different polymeric nanoparticle fabrication methods. These techniques generally involve polyelectrolyte complex formation, double emulsion/solvent evaporation techniques, or emulsion polymerization techniques. Spray drying is a process that uses jets of dissolved or suspended drug in an aqueous or other fluid phase that is forced through high pressure nozzles to produce a fine mist. Often, a bulking agent will be added to the fluid as well. The aqueous or other liquid contents of the mist evaporate, leaving behind a fine powder. A modification of spray drying, called air nebulization spray drying, uses two wedge-shaped nozzles through which compressed air passes and liquid solutions pass at high velocity. The wedge-shaped nozzle acts as a fluid acceleration zone where the four streams collide at high velocity, producing a shock wave that generates fine droplets. The droplets then descend into a column while being dried into a solid powder by heated air before being collected.

Stabilizers of interest include, without limitation, lecithin, which are naturally occurring mixtures of diglycerides of stearic, palmitic, and oleic acids, linked to the choline ester of phosphoric acid. Lecithin may be added to the first mixture, with the drug and oil. Other stabilizers of interest include, for example, cationic lipids, particularly phospholipids. A protein, such as albumin (for example bovine serum albumin, human serum albumin, etc.) may be used. Polyvinylpyrrolidone (PVP) is a water soluble branched polymer of N-vinylpyrrolidone, having a molecular weight of about 10K, and may be higher, e.g. from about 20K to 50K. Chitosan is a linear polysaccharide composed of randomly distributed β-(1,4) D-glucosamine and N-acetyl-D-glucosamine.

In some embodiments, the nanoparticles are stabilized with a mixture of albumin or other suitable protein, and a cationic lipid, e.g. in a ratio of about 1:15, 1:12, 1:11, 1:10; 1:9; 1:8, 1:5, etc. by weight. During formation of the nanoparticles, the stabilizer of the nanoparticles may be added to a suspension of the active agent before lyophilization.

The term "cationic lipids" is intended to encompass molecules that are positively charged at physiological pH, and more particularly, constitutively positively charged molecules, comprising, for example, a quaternary ammonium salt moiety. Cationic lipids used in the methods of the invention typically consist of a hydrophilic polar head group and lipophilic aliphatic chains. See, for example, Farhood et al. (1992) *Biochim. Biophys. Acta* 1111:239-246; Vigneron et al. (1996) *Proc. Natl. Acad. Sci.* (USA) 93:9682-9686.

Cationic lipids of interest include, for example, imidazolinium derivatives (WO 95/14380), guanidine derivatives (WO 95/14381), phosphatidyl choline derivatives (WO 95/35301), and piperazine derivatives (WO 95/14651). Examples of cationic lipids that may be used in the present invention include 1,2-distearoyl-sn-glycero-3-phosphocholine (DSPC); 1,2-dipalmitoyl-sn-glycero-3-phosphocholine (DPPC); DOTIM (also called BODAI) (Solodin et al., (1995) Biochem. 34: 13537-13544), DDAB (Rose et al., (1991) BioTechniques 10(4):520-525), DOTMA (U.S. Pat. No. 5,550,289), DOTAP (Eibl and Wooley (1979) Biophys. Chem. 10:261-271), DMRIE (Feigner et al., (1994) J. Biol. Chem. 269(4): 2550-2561), EDMPC (commercially available from Avanti Polar Lipids, Alabaster, Ala.), DCChoI (Gau and Huang (1991) Biochem. Biophys. Res. Comm. 179:280-285), DOGS (Behr et al., (1989) Proc. Natl. Acad. Sci. USA, 86:6982-6986), MBOP (also called MeBOP) (WO 95/14651), and those described in WO 97/00241.

The terms "aerosol," "particles," "aerosol particles," "aerosolized formulation" and the like are used interchangeably herein and shall mean particles of formulation comprised of pharmaceutically active drug and carrier which are formed for aerosol delivery, e.g. upon forcing the formulation through a nozzle using a jet or ultrasonic nebulizer. The terms "aerosol" and "aerosolized formulation," and the like, are used interchangeably herein to refer to a volume of air which has suspended within it particles of a formulation comprising a drug or diagnostic agent wherein the particles have a diameter in the range of 0.5 to 12 microns, for respiratory therapy, or in the range of 15 to 50 microns for ocular therapy, or in the range of 2 to 30 microns, preferably 10 to 20 microns, for nasal delivery.

The terms "formulation" and "flowable formulation" and the like are used interchangeably herein to refer to the active agent combined with a pharmaceutically acceptable carrier in flowable form having properties such that it can be aerosolized to particles for respiratory, nasal or ocular therapy. Such formulations are preferably solutions, e.g., aqueous solutions, ethanolic solutions, aqueous/ethanolic solutions, colloidal suspensions and microcrystalline suspensions.

The terms "particle diameter" and "diameter" are used when referring to the diameter of an aerosol particle and are defined as the "aerodynamic diameter". The "aerodynamic diameter" is the physical diameter of a sphere of unit density (1 gm/cm$^3$) that has the same terminal sedimentation velocity in air under normal atmospheric conditions as the particle in question. The deposition of aerosol particles in the bronchial airways of a human subject is described by a Stokes impaction mechanism which is characterized by a particles aerodynamic diameter. Thus, the diameter of one particle of material of a given density will be said to have the same diameter as another particle of the same material if the two particles have the same terminal sedimentation velocity in air under the same conditions.

The terms "ambient conditions," "ambient temperature," "ambient relative humidity" refer to the conditions of the air surrounding the patient and aerosol generation device, prior to this air being entrained into the device and being conditioned by the temperature controller.

The term "aerosol generation device" refers to any device for forming an aerosol for delivery to a human. These devices include but are not limited to systems that generate aerosols from liquid formulations, such as jet or ultrasonic nebulizers, spinning top generators, devices using an orifice or an array of orifices to form an aerosol (driven by a oscillation mechanism or not), and devices for the delivery of dry powder aerosols.

The term "drug delivery device" refers to a self contained portable device for the delivery of medication by way of inhalation. The term "container" is used herein to refer to a receptacle for holding and/or storing a drug formulation. The container can be single-dose or multidose, and/or disposable or refillable. The container may be refillable or a single use disposable container.

The contents of a container comprise a formulation, preferably a formulation of the active agent in either a flowable liquid or dissolved or dispersed in an excipient carrier, preferably without any additional material such as preservatives that might affect the patient. When the contents must be stored in a dry state, the package further includes another container that holds the liquid and can be combined with the dry drug immediately prior to administration.

The term "pharmaceutically acceptable" as used herein refers to a compound or combination of compounds that will not impair the physiology of the recipient human or animal to the extent that the viability of the recipient is compromised. Preferably, the administered compound or combination of compounds will elicit, at most, a temporary detrimental effect on the health of the recipient human or animal.

The term "carrier" as used herein refers to any pharmaceutically acceptable solvent of agents that will allow a therapeutic composition to be administered directly to the desired site, e.g. by inhalation. A "carrier" as used herein, therefore, refers to such solvents and compounds known to one of skill in the art that is pharmaceutically and physiologically acceptable to the recipient human or animal.

Formulation of Iron Chelating Nanoparticles

The formulations of the invention provide nanoparticles having a high concentration of an iron chelating agent for topical contact, usually for administration by aerosol with internal organs, which organs particularly include lungs. The formulation for administration is usually a suspension of iron chelator nanoparticles as defined above, usually a small molecule iron chelator, e.g. deferoxamine, deferiprone, deferasirox, and the like, in a carrier suitable for forming an aerosol that is biologically compatible, particularly compatible with tracheal tissue. The formulation is typically at least about 5%, 7.5% or 10% HIF-1α modulator nanoparticles, and not more than about 20%, 15%, or 12.5% HIF-1α modulator nanoparticles, where the balance is a physiologically compatible carrier.

Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

In one embodiment, the liposome-encapsulated iron chelating agent nanoparticle is administered to a patient in an aerosol inhalation device. Formulations of the invention can include iron chelating agent nanoparticle in combination with an amount of alveolar surfactant protein effective to enhance the transport of the liposomes across the pulmonary surface and into the circulatory system of the patient. U.S. Pat. No. 5,006,343, issued Apr. 9, 1991, which is incorporated herein by reference, disclosed formulations used in intrapulmonary delivery. Regardless of the form of the drug formulation, it is preferable to create droplets or particles for inhalation in the range of about 0.5 µm to 25 µm, from about 1 µm to 10 µm, from about 2-5 µm. By creating inhaled particles which have a relatively narrow range of size, it is possible to further increase the efficiency of the drug delivery system and improve the repeatability of the dosing. Thus in some embodiments the mean particle size may be within a narrow range so that 80% or more of the particles being delivered to a patient have a particle diameter which is within about 20% of the average particle size.

The formulations of the invention may be administered to a patient using a disposable package and portable, handheld, battery-powered device. Alternatively, the formulations of the instant invention may be carried out using a mechanical (non-electronic) device. Other inhalation devices may be used to deliver the formulations including conventional jet nebulizers, ultrasonic nebulizers, soft mist inhalers, dry powder inhalers (DPIs), metered dose inhalers (MDIs), condensation aerosol generators, and other systems.

An aerosol may be created by forcing drug through pores of a membrane which pores have a size in the range of about 0.25 to 6 microns. When the pores have this size the particles which escape through the pores to create the aerosol will have a diameter in the range of 0.5 to 12 microns. Drug particles may be released with an air flow intended to keep the particles within this size range. The creation of small particles may be facilitated by the use of the vibration device which provides a vibration frequency in the range of about 800 to about 4000 kilohertz. Those skilled in the art will recognize that some adjustments can be made in the parameters such as the size of the pores from which drug is released, vibration frequency, pressure, and other parameters based on the density and viscosity of the formulation.

The viscosity of the drug by itself or in combination with a carrier should be sufficiently low so that the formulation can be forced out of openings to form an aerosol, e.g., using 20 to 200 psi to form an aerosol, for example having a particle size in the range of about 0.5 to 25 microns.

In an embodiment, a low boiling point, highly volatile propellant is combined with the nanoparticles of the invention and a pharmaceutically acceptable excipient. The nanoparticles may be provided as a suspension or dry powder in the propellant, or, in another embodiment, the nanoparticles are dissolved in solution within the propellant. Both of these formulations may be readily included within a container which has a valve as its only opening. Since the propellant is highly volatile, i.e. has a low boiling point, the contents of the container will be under pressure.

In accordance with another formulation, the iron chelating agent nanoparticles are provided as a dry powder, and in accordance with still another formulation, the iron chelating agent nanoparticles are provided in a solution formulation. The dry powder may be directly inhaled by allowing inhalation only at the same measured inspiratory flow rate and inspiratory volume for each delivery. The powder may be dissolved in an aqueous solvent to create a solution which is moved through a porous membrane to create an aerosol for inhalation. Any formulation which makes it possible to produce aerosolized forms of iron chelating agent nanoparticles which can be inhaled and delivered to a patient via the intrapulmonary route may be used in connection with the present invention.

Based on the above, it will be understood by those skilled in the art that a plurality of different treatments and means of administration can be used to treat a single patient. Some patients may receive only iron chelating agent nanoparticle formulations by inhalation. Such patients may have symptoms of a graft rejection episode, or have symptoms of a medical condition, which symptoms may benefit from administration to the patient of the iron chelating agent nanoparticle.

This dose will typically be administered by at least one, preferably several "puffs" from the aerosol device. The total dose per day is preferably administered at least once per day, but may be divided into two or more doses per day. Some patients may benefit from a period of "loading" the patient with a higher dose or more frequent administration over a period of days or weeks, followed by a reduced or maintenance dose.

Specific information regarding formulations which can be used in connection with aerosolized delivery devices are described within Remington's Pharmaceutical Sciences, A. R. Gennaro editor (latest edition) Mack Publishing Company. For a brief review of methods for drug delivery, see, Langer, Science 249:1527-1533 (1990).

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from cell culture and/or animal studies can be used in formulating a range of dosages for humans. The dosage of the active ingredient typically lines within a range of circulating concentrations that include the $ED_{50}$ with low toxicity. The dosage can vary within this range depending upon the dosage form employed and the route of administration utilized.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

The compositions of the invention may be administered using any medically appropriate procedure. The effective amount of a therapeutic composition to be given to a particular patient will depend on a variety of factors, several of which will be different from patient to patient. A competent clinician will be able to determine an effective amount of a therapeutic agent. The compositions can be administered to the subject in a series of more than one administration, or preferably is administered to the target tissue during periods of chronic graft rejection episodes.

Those of skill will readily appreciate that dose levels can vary as a function of the specific compound, the severity of the symptoms and the susceptibility of the subject to side effects. Some of the drugs are more potent than others. Preferred dosages for a given agent are readily determinable by those of skill in the art by a variety of means. A preferred means is to measure the physiological potency of a given compound.

Administration

Following transplantation of a solid organ, particularly lung transplantation, there can be episodes in which an immune response is mounted against the organ. During such episodes, the transplanted tissue is stressed and may suffer diminished function. The function of the transplanted tissue is improved by administration of an iron chelating agent in a nanoparticle formulation, which improves the state of the microvasculature at the site of the rejection episode.

Chronic rejection explains long-term morbidity in most lung-transplant recipients, the median survival roughly 4.7 years, about half the span versus other major organ transplants. In histopathology the condition is bronchiolitis obliterans, which clinically presents as progressive airflow obstruction, often involving dyspnea and coughing, and the patient eventually succumbs to pulmonary insufficiency or secondary acute infection. Airflow obstruction not ascribable to other cause is labeled bronchiolitis obliterans syndrome (BOS), confirmed by a persistent drop over three or more weeks in forced expiratory volume ($FEV_1$) by at least 20%. BOS is seen in over 50% of lung-transplant recipients by 5 years, and in over 80% by ten years. First noted is infiltration by lymphocytes, followed by epithelial cell injury, then inflammatory lesions and recruitment of fibroblasts and myofibroblasts, which proliferate and secrete proteins forming scar tissue. BOS progression varies widely: lung function may suddenly fall but stabilize for years, or rapidly progress to death within a few months. Risk factors include prior acute rejection episodes, gastroesophageal reflux disease, acute infections, particular age groups, HLA mis-matching, lymphocytic bronchiolitis, and graft dysfunction (e.g., airway ischemia).

Diagnosis of a rejection episode may utilize on clinical data, markers for activation of immune function, markers for tissue damage, and the like. Histological signs include: infiltrating T cells, perhaps accompanied by infiltrating eosinophils, plasma cells, and neutrophils, particularly in telltale ratios, structural compromise of tissue anatomy, varying by tissue type transplanted, and injury to blood vessels. Tissue biopsy is restricted, however, by sampling limitations and risks/complications of the invasive procedure. Cellular magnetic resonance imaging (MRI) of immune cells radiolabeled in vivo may provide noninvasive testing.

The formulations of the present invention are administered to the affected tissue upon an initial indication of a rejection episode, and may be maintained for a period of time; e.g. about 1 day, 2 days, 3 days, 4 days, 5 days, 6 days, 1 week, 10 days, 2 weeks, 3 weeks, etc. as needed. Administration may be as frequent as needed, e.g. hourly, about 3 to 4 hours, semi-daily, daily, etc.

The formulations of the invention may be administered in conjunction with conventional treatment for a graft rejection episode, particularly immunosuppressive drugs such as cyclosporine A, corticosteroids, methotrexate, etc. as known in the art.

Of particular interest is topical application of the formulation to the trachea and lungs during a rejection episode The transient upregulation of HIF1α activity improves the vascularization of the graft, providing for improved long term graft function.

Kits and Packaging

In some embodiments, formulations are provided for use in the methods of the invention. Such formulations may comprise a stabilized nanoparticle of an iron chelating agent, including without limitation DFO, DFX, DFP, etc., which can be provided in a packaging suitable for clinical use, including packaging as a lyophilized, sterile powder; packaging of a stable suspension of active agent, for example nanoparticles, in carrier; separate packaging of nanoparticles and carrier suitable for mixing prior to use; and the like. The packaging may include an inhaler. The packaging may be a single unit dose, providing an effective dose of an iron chelator active agent in nanoparticle form in the manufacture of a medicament for improving the function of a solid organ transplant, wherein the medicament is topically applied to the surface of tissues at the site of anastomosis, usually immediately prior to, or at the time of transplantation surgery.

EXPERIMENTAL

HIF-1 and Lung Transplantation

The main limitation to long-term survival of a lung transplant is chronic rejection, which is manifested by a terminal airway fibrotic process that presents clinically as the bronchiolitis obliterans syndrome (BOS). The cumulative incidence of BOS within 6 years of transplantation is greater than 50%. Despite identification of risk factors such as acute cellular rejection, lymphocytic bronchitis/bronchiolitis, and CMV infection, the mechanisms by which BOS develops remain elusive. Recent autopsy studies reveal a marked loss of microvasculature in the pre-obliterative bronchiolitis (pre-OB) foci of human lung transplants, which suggests that a loss of microcirculation and airway ischemia precede the onset of OB. Clinical studies from other solid organ transplants, such as liver and kidney, also demonstrate that chronic rejection develops after a loss of functional microvasculature. In a preclinical model of lung transplantation, it has been have shown that without immunosuppression, acute rejection eventually results in rejection of the donor microvasculature and a complete cessation of blood flow to the transplant. In this model, the presence of a functional microvasculature is essential for airway allografts to be rescued with immunosuppression from chronic rejection. These clinical and preclinical findings cumulatively suggest that loss of the microvascular circulation may be a fundamental cause of chronic rejection. However, little is known about how microvessels are altered by rejection and whether manipulation of this process can change the final outcomes of acute rejection episodes.

Ischemia is the principal stimulus that induces neovascularization. Expression of virtually all proangiogenic growth factors is induced by hypoxia through the transcriptional activity of HIF-1. HIF-1 is a heterodimer composed of a constitutively expressed HIF-1β subunit and an oxygen-regulated HIF-1α subunit. AdCA5, an adenovirus vector encoding a constitutively active form of HIF-1α, has been demonstrated in several animal models to promote angiogenesis and accelerate recovery from tissue ischemia. HIF-1-mediated transcriptional responses orchestrate the expression of proangiogenic growth factors that facilitate angiogenesis by directly activating resident endothelial cells as well as recruiting circulating angiogenic cells. Tie2 is a promoter that has been used to identify several subpopulations of cells that participate in neovascularization. Mice expressing the GFP or LacZ transgene under the control of Tie2 have proven useful in tracking the fate of heterogeneous and migrating cell populations (e.g., CD45-CD31+ endothelial cells, Tie2-expressing monocytes [TEMs]), which participate in new vessel formation.

Several animal models, including orthotopic tracheal transplant (OTT), heterotopic tracheal transplant, and orthotopic lung transplant, have been used to study the pathology associated with human lung transplantation. To date, rodent models have not convincingly replicated OB lesions. However, although OTT does not develop the clinically relevant airway obliteration, it reproducibly develops subepithelial fibrosis and mimics the clinically relevant pathology of lymphocytic bronchitis, a large airway correlate of BOS. Moreover, the OTT model is an ideal system to study airway microvascular repair and remodeling that occurs during alloimmune injury because of the well-organized planar anatomy of airway microvasculature. OTT accurately models transplantation-associated changes in the large airways, an area of tissue that is temporarily devitalized because the bronchial artery circulation (which conducts blood with high pO2 from the aorta) is not usually surgically restored at the time of transplantation.

OTTs undergoing acute rejection are relatively hypoxic compared with nonrejecting tracheal tissue, and undergo sequential damage characterized first by microvascular injury, followed by airway ischemia, and finally, reperfusion with active neovascularization. Recent clinical studies revealed that human lung transplant airways also are relatively hypoxic at baseline compared with both native (diseased) and control airways. During rejection increased hypoxia and ischemia may trigger an adaptive response to promote neovascularization of the allograft through activation of HIF-1α. HIF-1α consequently may be one of the central factors that help to maintain a functional microvasculature in transplanted organs.

Time-dependent microvascular changes that occur during allograft rejection were carefully characterized, focusing on how the donor and recipient tissues interact with each other to facilitate vascular recovery. The normal role that Hif1a plays in the repair of the damaged microvasculature of an OTT was examined. The main objective for these experiments was to determine whether limiting airway hypoxia and ischemia, through enhanced maintenance or accelerated recovery of the airway microvasculature, could prevent chronic rejection.

Methods of preserving a functional microvasculature were studied, using efforts to delay donor loss of functional microvasculature by efforts to promote donor microvasculature integrity. To begin with, upon comparison of chronically rejected transplanted to native microvasculature, it was found that the normal high level of organization in the native tissue was not present in the grafted tissue. In fact, microvascularization was only partial and the vessels were of a different form. The disorganization of the transplanted vessels made them appear similar to tumor microvasculature, suggesting that the vessels were immature and unstable.

Efforts to accelerate recovery through increased growth of recipient vessels were also used. It was found that recipient cells were actively involved in promoting donor microvasculature integrity. Thus, recipient-derived cells prominently contribute to the remodeling of the microvasculature of OTTs undergoing chronic rejection.

The involvement of recipient-derived Tie2 cells in allograft preservation was also studied. Previously, successful kidney transplants showed replacement of donor-derived epithelial cells by recipient-derived Tie2 cells, suggesting that these cells help repair the injuries present in the donor tissue. It has now also been shown that this replacement of donor endothelial cells by recipient endothelial cells is present to a high degree in remodeling of the microvasculature of OTTs undergoing chronic rejection. In fact, the recipient blood vessels are a major source of reestablished vessels in chronic rejection, and these blood vessels are functional.

Transient HIF-1α gene overexpression prolongs microvascular perfusion of airway allograft and alleviates tissue hypoxia. HIF-1α deficiency led to an accelerated loss of airway microvasculature. Therefore, application of a HIF-1 potentiating agent was studied by particulate delivery directly to the host tissue.

Materials and Methods

Mice.

All animal procedures were approved by Stanford's Administrative Panel on Laboratory Animal Care (APLAC) and/or the VA Palo Alto Institutional Animal Care and Utilization Committee (IACUC). All mice including C57BL/6J (B6; H-$2^b$), Balb/C (H-$2^d$), FVB/NJ (H-$2^q$), FVB/N-Tg (TIE2-lacZ) 182Sato/J, FVB-Tg (TIE2GFP287Sato/J), B6.Cg-Tg (Tek-cre) 12Flv/J, B6.129X1-Gt(ROSA)26Sortm1(EYFP)Cos/J, B6.Cg-Tg(CAG-cre/Esr1*)5Amc/J, and B6.129-Hif1atm3Rsjo/J were purchased from the Jackson Laboratory. For Tie2 lineage-tracing studies, ROSA26EYFP reporter mice were crossed with mice expressing Tie2-Cre. To create Hif1a CKO, mice with loxP sites on both sides of exon 2 of the Hif1a gene (Hif1$^{loxP/loxP}$) were crossed with mice expressing tamoxifen-inducible Cre recombinase under the control of the CAG promoter (Cag-Cre-ER). Mice with the transgenes Cag-Cre-ER, Hif1$^{WT/WT}$, and Cag-Cre-ER, Hif1$^{loxP/loxP}$, were used as control and Hif1a CKO respectively. Mice carrying Cag-Cre-ER and floxed Hif1a genes were treated with tamoxifen for 5 consecutive days at a dose of 120 mg/kg followed by at least 2 more days to allow sufficient recombination prior to their use in studies. Tamoxifen, which activates the Cre recombinase, efficiently recombined the Hif1a gene.

Tracheal Transplantation.

Basic procedure: seven-ring tracheal segments were removed from CO2-euthanized donor mice that were matched for recipient age and male sex. Recipient mice were anesthetized with ketamine 50 mg/kg ketamine and 10 mg/kg xylazine, and a short incision was made in the midline neck region. Division of the strap muscles allowed visualization of the entire laryngotracheal complex. After the recipient's trachea was transected, the donor trachea was sewn in with 10-0 nylon sutures, and the overlying skin was closed with 5-0 silk.

Immunosuppression and Drug Therapy.

The immunotherapy protocol was identical to a previously published study using combined anti-LFA-1/anti-CD40L therapy. Animals received the following protocol: anti-LFA-1 (KBA), 200 μg i.p. on days 0, 1, 7, and 14 (day 0 being the day of transplantation), and anti-CD40L (MR-1), 250 μg i.p. on day 1 and twice per week thereafter. VEGFR2 antagonist SU5416 from SUGEN (now Pfizer, NY, N.Y.) was dissolved in CMC (carboxymethylcellulose) and administered at 20 mg/kg subcutaneously every other day for the study period. A hexapeptide CXCR2 antagonist known as antileukinate was dissolved in Hanks buffered saline solution to a concentration of 8 mg/ml and administered using an Alzet (Cupertino, Calif.) microosmotic pump implanted subcutaneously on the day of transplant at a rate of 0.25 μl per hour, delivering 2 μg of drug per hour.

Histology.

For axial sections, tracheae were sagittally divided, with one half being formalin fixed (H&E; trichrome) and one-half frozen for immunohistochemistry. Paraffin-embedded tracheal segments were initially fixed in cold 10% neutral-buffered formalin solution, and 5-μm sections were cut and stained for H&E and Masson's trichrome. For immunohistochemistry studies, 5-μm frozen sections were used. Endothelial cells were identified by CD31 immunoreactivity using rat anti-mouse CD31 (BD Biosciences). For class I MHC staining, mouse anti-mouse H-2Kd (BD Biosciences) was used. An Olympus BX51 microscope with Image-Pro Plus Image Analysis Software (Media Cybernetics, MD) and camera were used for histological and orphometric analysis. Double staining for β-galactosidase and CD31 involved the standard β-galactosidase as used below for whole mounts followed by the CD31 immunostaining technique followed above. C3 staining was conducted on frozen sections using either FITC-conjugated goat anti-mouse C3 antibody or goat anti-mouse C3 primary antibody (MP Biomedicals, CA) and a Cy3 rabbit anti-goat secondary antibody (Jackson ImmunoResearch Laboratories Inc., Bar Harbor, Me.).

Whole-Mount Tissue Fixation, Harvest, and Staining.

Whole-mount tracheae were evaluated for vascular perfusion and CD31 immunoreactivity by fluorescence staining techniques as described previously by Baffert et al. Detailed methods were provided by Donald McDonald (UCSF, San Francisco, Calif., USA). Under anesthesia, 100 μl of 1 mg/ml FITC-conjugated *Lycopersicon esculentum* tomato lectin (Vector Laboratories, Burlingame, Calif.) was injected into the inferior vena cava over 1 minute. After 3 minutes of circulation, sternotomy was performed followed by right atriotomy and cannulation of the aorta via left ventricle with an 18 gauge angiocatheter. PBS with 1% paraformaldehyde was perfused via the aorta for 2 minutes at 120 mmHg. Orthotopic tracheal graft along with adjoining recipient trachea was dissected free of surrounding tissues. The trachea was pinned and incubated in 1% paraformaldehyde. Following a PBS wash, the trachea was bathed in 5% donkey serum (Jackson ImmunoResearch Laboratories Inc., Bar Harbor Me.) and in PBS+ (PBS containing 0.1% Triton X-100 and 0.2% albumin). Blocking serum was poured off, and PBS+ containing rat anti-PECAM-1 (CD31) (BD Biosciences) and 1% donkey serum was added and incubated. Tracheae were then washed in PBS+ and in Cy3-conjugated donkey anti-rat secondary antibody (Jackson Immunoresearch) in PBS+ with no serum and incubated. Whole tracheae were placed on glass slides in Vectashield H1000 anti-quench mounting medium (Vector Laboratories, Burlingame, Calif.) and a coverslip placed.

Confocal Microscopy.

Images were acquired on a Zeiss LSM510 laser scanning confocal microscope located in the Light Microscopy Core Facility at the University of Colorado. A software configuration was established to simultaneously capture emission wavelengths from the FITC-conjugated lectin and the Cy3-conjugated secondary antibody used to detect CD31 antigen. Images were captured using a Zeiss 20× Plan-Apochromat objective with a numerical aperture of 0.8 and a working distance of 0.55 mm. The x-y resolution was 0.45 μm and the z-stacks were acquired at 2-μm intervals. The pinholes for the PMT detectors were optimized to 1 airy disk.

β-Galactosidase Vessel Origin Study.

To identify recipient blood vessels, we used FVB/N-Tg (Tie2-lacZ)182Sato/J mice (Jackson Laboratory, Bar Harbor, Me.), which carry reporter gene β-galactosidase under control of the Tie2 (a promoter that identifies vascular endothelium). They were transplanted with tracheae from MHC-matched FVB and MHC-mismatched BALB/c donors. Allogeneic and syngeneic grafts were harvested as whole mounts as described above following 1% PFA in PBS vascular fixation. They were then soaked in 1% PFA in PBS at 4° C. for 60 minutes. β-Galactosidase expressing vessels were stained blue using X-Gal Staining kit (Millipore, Billarica Pa.; Chemicon) per the manufacturer's protocol. After rinsing in PBS, tracheae were placed on glass slides with aqueous mounting medium Aqua-Mount (Fisher Scientific, worldwide) and then compressed with coverslips and 5 ounces lead weight and allowed to dry. As above, Olympus BX51 microscope and camera were used to acquire photomicrographs.

Tissue Oximetry.

Tissue oxygen content was measured by fluorescence quenching technique using OxyLab pO2 monitor (Oxford Optronix Ltd., Oxford, UK) fiber optic probe mounted to a micromanipulator. Trachea was exposed on an anesthetized animal, and 23 gauge needle was used to make an opening in the anterior wall of the trachea. The fiber-optic probe was inserted at a 45° C. angle to contact the epithelium of the opposite side wall of the trachea. The probe was lowered until it placed gentle pressure on the wall and pO2 reading reduced to 5 mmHg or less (signaling compression of tissue). It was then raised at approximately 20-μm increments. The stable pO2 reading, prior to a rapid rise to at least 60 mmHg that signaled loss of tissue contact, was used as the tissue oxygen partial pressure.

EM Studies.

Tracheal allografts were excised and fixed in 1.5% glutaraldehyde in 0.1M cacodylate buffer instilled through the trachea at 23 cm pressure for 24 hours. Samples were washed with 0.1M cacodylate buffer, postfixed in 1% OsO4 buffered with 0.1M cacodylate buffer for 1 hour, washed again with 0.1M cacodylate buffer, and stained with 3% uranyl acetate for 30 minutes. Samples were then dehydrated with grade acetone and embedded in plastic. Cut sections were viewed with a Philips CM10 electron microscope and photographed (Advanced Microscopy Techniques).

Western Blotting.

Liquid nitrogen-cooled tracheas were pulverized with a liquid nitrogen-cooled BioPulverizer. Powdered tracheas were hand-homogenized in 70 μl of RIPA buffer with both protease and phosphatase inhibitors (Thermo Fisher Scientific). Extracts were incubated on ice for 30 minutes, followed by centrifugation at 4° C. for 15 minutes at 18,000 g. Extracts containing 35 μg protein were separated on SDS gels and transferred to nitrocellulose membranes. Actin was used as an internal control. Membranes were incubated with anti-HIF-1α (Novus), anti-SDF-1 (R&D), or anti-actin (Sigma-Aldrich) at 4° C. overnight. Blots were incubated with the appropriate secondary antibodies and signals were detected by PhosphorImager analysis using ECL Plus (Amersham)

Delayed Immunotherapy Experiments.

To determine whether the duration of rejection had any effect on the ability to prevent airway remodeling in acutely rejecting airways, B6 mice underwent tracheal transplant from BALB/c donors. Rejecting grafts were excised from the original recipient. Tracheae were retransplanted orthotopically into immunologically naive B6 mice that received immunotherapy with anti-LFA-1/anti-CD40L as described above. These grafts were re-excised 28 days following retransplantation for histologic examination.

Morphometric Analysis.

Assessment for airway remodeling was performed using a ratio of subepithelial height to epithelial height. We have previously validated this measure as having a high degree of correlation with a chronic rejection scoring system. Image-Pro Plus Image Analysis Software (Media Cybernetics, Bethesda, Mass.) was used to make 3 measurements of each variable in each specimen. Vessel number quantification was performed on axial tracheal sections with CD31 immunostain by counting total numbers of independent CD31+ structures per entire tracheal ring (n=5 per group). Tracheal whole mounts perfused with FITC-conjugated tomato lectin were assessed for mean fluorescent intensity using Intelligent Imaging Innovations Slide-Book software. The same software was used to created masks based on a fixed FITC threshold to mask perfused blood vessels. The percentage of area in the mask as compared with total area was measured to create an index of vessel area. Three measurements were made from each specimen.

Statistics.

Intergroup statistical analysis was performed using 1-way ANOVA with a Tukey post-test for a significance level of $P<0.05$.

Deferasirox (DFX) was obtained from Bachem, Switzerland, deferoxamine mesylate (DFO) and L-leucine were purchased from Sigma-Aldrich, USA, 1,2-distearoyl-sn-glycero-3-phosphocholine (DSPC), 1,2-dipalmitoyl-sn-glycero-3-phosphocholine (DPPC) were purchased from Corden Pharma, USA. All the solvents used were of reagent grade.

Formulations of inhalable DFX and DFO contain by weight 43% of the drug, 35% of l-leucine, and 11% each of DPPC and DSPC. To prepare the solutions, first L-Leucine was moistened with four times by volume of 2 N NaOH, and ethanol was added drop-wise until a clear solution was obtained. For DFO formulation, the drug, DPPC and DSPC were all dissolved in ethanol and added to the L-Leucine solution. For DFX formulation, DFX was first dissolved in solvent mixture containing ethanol and acetone 3:20 by volume, and DSPC and DPPC were dissolved in ethanol and added to the final mixture. Control formulations containing 63% of L-leucine, 19.3% each of DPPC and DSPC were prepared by same method as DFO formulation.

All the formulations were spray dried using Buchi B-290 mini spray dryer, with inlet temperature at 120° C., aspirator at 35 m3/hour, feed pump at 3 mL/min and Nitrogen flow rate at 0.473 m3/hour.

All the collected particles were characterized using Scanning Electron Microscopy (SEM). All the particles were coated with 7 nm thick Au—Pd layer using a Denton Desktop II sputter coater, and imaged in Hitachi 3700 VP-SEM under secondary electron mode at the Cell Sciences Imaging Facility (CSIF), Stanford.

Example 2

Preparation of Particles

Particles were prepared by dissolving lecithin in ethanol; and dissolving leucine and DFO in 6N HCl and water at pH 2. The lecithin solution was added dropwise into the DFO solution with rapid stirring. The resulting solution was sprayed over a Teflon sheet and allowed to dry overnight at 37° C. After drying, the particles were collected and deep dried by high vacuum. For particle compositions, the following formulations were tested:

TABLE 1

| | % (mg) | | | Solvents (ml) | | |
|---|---|---|---|---|---|---|
| | Lecithin | L-Leucine | DFO | EtOH (mL) | Water (mL) | 6N HCl (mL) |
| Particle #1 | 21.7(100) | 34.8(160) | 43.5(200) | 1.0 | 4.9 | 0.12 |
| Particle #2 | 16.1(100 | 51.6(320) | 32.3(200) | 8.0 | 2.6 | 0.4 |
| Particle #3 | 11.1(50) | 66.7(300) | 22.2(100) | 1.5 | 3.7 | 0.32 |

In a second set of formulations, leucine and DFO were dissolved in 1N NaOH and water (pH=9). Then, 2 ml EtOH was added drop by drop. 1,2-distearoyl-sn-glycero-3-phosphocholine (DSPC) and/or 1,2-dipalmitoyl-sn-glycero-3-phosphocholine (DPPC) were dissolved in EtOH. The lipid solution was added drop wise into the DFO solution with rapid stirring. This solution was sprayed over the Teflon sheet at 37° C. and left it overnight to dry. The particles were collected and deep dried by high-vacuum.

TABLE 2

|  | % (mg) | | | | Solvents (mL) | |
| --- | --- | --- | --- | --- | --- | --- |
| | DSPC | DPPC | L-Leucine | DFO | EtOH | Water | 1N NaOH |
| Particle #4 | 11(5) | 11(5) | 35(16) | 43(19.5) | 4.0 | 0.13 | 0.12 |
| Particle #5 | 0 | 22(10) | 35(16) | 43(19.5) | 4.0 | 0.13 | 0.12 |
| Particle #6 | 22(10) | 0 | 35(16) | 43(19.5) | 3.5 | 0.13 | 0.12 |

In an alternative method, leucine was dissolved in 1N NaOH and water (pH=9). Then, 20 ml ethanol was added drop by drop. The lipids (CSPC, DPPC) were dissolved in ethanol and added dropwise to the aqueous solution with stirring. The resulting solution was dried by rotary evaporator. The solids were then collected and deep dried by high vacuum.

TABLE 3

|  | % (mg) | | | | Solvents (ml) | |
| --- | --- | --- | --- | --- | --- | --- |
| | DSPC | DPPC | Leu | DFX | EtOH | Water | 1N NaOH |
| Particle #7 | 11(110) | 11(110) | 35(350) | 43(430) | 43 | 2.85 | 2.6 |
| Particle #8 | 0 | 22(220) | 35(350) | 43(430) | 43 | 2.85 | 2.6 |
| Particle #9 | 22(220) | 0 | 35(350) | 43(430) | 43 | 2.85 | 2.6 |

Particle generation. Conventional thin film hydration method results in very poor hydrophilic drug entrapment. Drug entrapment by sponging the freeze dried liposome have the limitation of specific lipid selection or inclusion of sugars in the formulations. The methods of the present invention address these issues by dissolving all the components as soluble free-flowing solutions, and generating particles by nebulizing from air and allowing to fall over a hydrophobic surface by gravity, or spraying under a vacuum using a rotary evaporator.

Example 3

Deferoxamine and Deferasirox Nanocapsule Formulations

| DFO1: | | | | | |
| --- | --- | --- | --- | --- | --- |
| A DFO | B Lecithin | C Polaxamer-188 (0.5% Aq.) | D Chitosan-5K (0.5% Aq.) | E Labrafac CC | F PVP-10K (40% Aq.) |
| %19.75 mg 200 | 19.75 200 | 19.75 200 (40 ml) | 1.23 12.5 (2.5 ml) | 29.63 300 | 9.88 100 (2.5 ml) |

DFO nanocapsules were prepared by a series mixing steps under stirring and bath sonication conditions followed by deep freezing and freeze drying. Briefly, 200 mg of DFO, 200 mg of lecithin and 300 mg of labrafac lipophile were mixed to form a first mixture; then 40 mL of 0.5% aqueous solution of Polaxamer-188 were added to form a first homogeneous liquid; 2.5 mL of 0.5% aqueous solution of chitosan-5K were added to form a second homogeneous liquid followed by adding 2.5 mL of 40% aqueous solution of PVP-10K to form a final homogeneous liquid. The final homogeneous liquid was freeze dried to obtain dry nanocapsules.

| BLA1: | | | | | |
| --- | --- | --- | --- | --- | --- |
| A DFO | B Lecithin | C Polaxamer-188 (0.5% Aq.) | D Chitosan-5K (0.5% Aq.) | E Labrafac CC | F PVP-10K (40% Aq.) |
| %0 mg 0 | 24.62 200 | 24.62 200 (40 ml) | 1.54 12.5 (2.5 ml) | 36.92 300 | 12.31 100 (2.5 ml) |

The blank nanocapsules were prepared without DFO.

| DFX1 | | | | | |
| --- | --- | --- | --- | --- | --- |
| A DEF | B Lecithin | C Polaxamer-188 (0.5% Aq.) | D Chitosan-5K (0.5% Aq.) | E Labrafac CC | F PVP-10K (40% Aq.) |
| %19.75 mg 200 | 19.75 200 | 19.75 200 (40 ml) | 1.23 12.5 (2.5 ml) | 29.63 300 | 9.88 100 (2.5 ml) |

DFX nanocapsules were prepared by a series mixing steps under stirring and bath sonication conditions followed by deep freezing and freeze drying. Briefly, a mixture of DFX and lecithin was obtained by dissolving 200 mg of DEX and 200 mg of lecithin in 10 mL of methanol/acetone (1:10) followed by removal of solvents in a rotary evaporator; then 40 mL of 0.5% aqueous solution of Polaxamer-188 and 300 mg of labrafac lipophile were added to form a first homogeneous liquid; 2.5 mL of 0.5% aqueous solution of chitosan-5K were added to form a second homogeneous liquid followed by adding 2.5 mL of 40% aqueous solution of PVP-10K to form a final homogeneous liquid. The final homogeneous liquid was freeze dried to obtain dry nanocapsules.

| DFO2: | | | | | |
|---|---|---|---|---|---|
| A<br>DFO | B<br>Lecithin | C<br>Polaxamer-188<br>(0.5% Aq.) | D<br>Probumin<br>(0.5% Aq. | E<br>Labrafac<br>CC | F<br>PVP-10K<br>(40% Aq.) |
| %19.75<br>mg 200 | 19.75<br>200 | 19.75<br>200 (40 ml) | 1.23<br>12.5 (2.5 ml) | 29.63<br>300 | 9.88<br>100 (2.5 ml) |

DFO nanocapsules were prepared by a series mixing steps under stirring and bath sonication conditions followed by deep freezing and freeze drying. Briefly, 200 mg of DFO, 200 mg of lecithin, and 300 mg of labrafac lipophile were mixed to form a first mixture; then 40 mL of 0.5% aqueous solution of Polaxamer-188 were added to form a first homogeneous liquid; 2.5 mL of 0.5% aqueous solution of probumin were added to form a second homogeneous liquid followed by adding 2.5 mL of 40% aqueous solution of PVP-10K to form a final homogeneous liquid. The final homogeneous liquid was freeze dried to obtain dry nanocapsules.

| BLA2: | | | | | |
|---|---|---|---|---|---|
| A<br>DFO | B<br>Lecithin | C<br>Polaxamer-188<br>(0.5% Aq.) | D<br>Probumin<br>(0.5% Aq. | E<br>Labrafac<br>CC | F<br>PVP-10K<br>(40% Aq.) |
| %0<br>mg 0 | 24.62<br>200 | 24.62<br>200 (40 ml) | 1.54<br>12.5 (2.5 ml) | 36.92<br>300 | 12.31<br>100 (2.5 ml) |

The blank nanocapsules were prepared without DFO.

| 6.DFX2: | | | | | |
|---|---|---|---|---|---|
| A<br>DEF | B<br>Lecithin | C<br>Polaxamer-188<br>(0.5% Aq.) | D<br>Probumin<br>(0.5% Aq. | E<br>Labrafac<br>CC | F<br>PVP-10K<br>(40% Aq.) |
| %19.75<br>mg 200 | 19.75<br>200 | 19.75<br>200 (40 ml) | 1.23<br>12.5 (2.5 ml) | 29.63<br>300 | 9.88<br>100 (2.5 ml) |

DFX nanocapsules were prepared by a series mixing steps under stirring and bath sonication conditions followed by deep freezing and freeze drying. Briefly, a mixture of DFX and lecithin was obtained by dissolving 200 mg of DFX and 200 mg of lethicin in 10 mL of methanol/acetone (1:10) followed by removal of solvents in a rotary evaporator; then 40 mL of 0.5% aqueous solution of Polaxamer-188 and 300 mg of labrafac lipophile were added to form a first homogeneous liquid; 2.5 mL of 0.5% aqueous solution of probumin were added to form a second homogeneous liquid followed by adding 2.5 mL of 40% aqueous solution of PVP-10K to form a final homogeneous liquid. The final homogeneous liquid was freeze dried to obtain dry nanocapsules.

| DFO3: | | | | |
|---|---|---|---|---|
| A<br>DFO | B<br>Lecithin | C<br>Polaxamer-188<br>(0.5% Aq.) | D<br>Probumin<br>(0.5% Aq. | E<br>Labrafac CC |
| %21.92<br>mg 200 | 21.92<br>200 | 21.92<br>200 (40 ml) | 1.37<br>12.5 (2.5 ml) | 32.88<br>300 |

DFO 3 nanocapsules were prepared by a series mixing steps under stirring and bath sonication conditions followed by deep freezing and freeze drying. Briefly, 200 mg of DFO, 200 mg of lecithin, and 300 mg of labrafac lipophile were mixed to form a first mixture; then 40 mL of 0.5% aqueous solution of Polaxamer-188 were added to form a first homogeneous liquid; 2.5 mL of 0.5% aqueous solution of probumin were added to form a second homogeneous liquid. The second homogeneous liquid was freeze dried to obtain dry nanocapsules.

| BLA3: | | | | |
|---|---|---|---|---|
| A<br>DFO | B<br>Lecithin | C<br>Polaxamer-188<br>(0.5% Aq.) | D<br>Probumin<br>(0.5% Aq. | E<br>Labrafac CC |
| %0<br>mg 0 | 28.01<br>200 | 28.01<br>200 (40 ml) | 1.75<br>12.5 (2.5 ml) | 42.1<br>300 |

The blank nanocapsules were prepared as same as DFO3 nanocapsules without DFO.

| DFX3: | | | | |
|---|---|---|---|---|
| A<br>DEX | B<br>Lecithin | C<br>Polaxamer-188<br>(0.5% Aq.) | D<br>Probumin<br>(0.5% Aq. | E<br>Labrafac CC |
| %21.92<br>mg 200 | 21.92<br>200 | 21.92<br>200 (40 ml) | 1.37<br>12.5 (2.5 ml) | 32.88<br>300 |

DFX3 nanocapsules were prepared by a series mixing steps under stirring and bath sonication conditions followed by deep freezing and freeze drying. Briefly, a mixture of DFX and lecithin was obtained by dissolving 200 mg of DFX and 200 mg of lecithin in 10 mL of methanol/acetone (1:10) followed by removal of solvents in a rotary evaporator; then 40 mL of 0.5% aqueous solution of Polaxamer-188 and 300 mg of labrafac lipophile were added to form a first homogeneous liquid; 2.5 mL of 0.5% aqueous solution of probumin were added to form a second homogeneous solution. The final homogeneous solution was freeze dried to obtain dry nanocapsules.

Example 4

Deferoxamine (DFO) Nanoparticles Alleviate Airway Ischemia

Airway tissue ischemia and hypoxia in human lung transplantation is a consequence of the sacrifice of the bronchial circulation during the surgical procedure and is a major risk factor for the development of airway anastomotic complications. Augmented expression of HIF-1α promotes microvascular repair and alleviates allograft ischemia and hypoxia. DFO is an FDA-approved iron chelator which has been shown to upregulate cellular HIF-1α. Here, we developed a nanoparticle formulation of DFO that can be topically applied to airway transplants. In a mouse OTT model, the DFO nanoparticle was highly effective in enhancing airway microvascular perfusion following transplantation through the production of the angiogenic factors, placental growth factor (PLGF) and stromal cell-derived factor (SDF)-1. The endothelial cells in DFO treated airways displayed higher levels of p-eNOS and Ki67, less apoptosis, and decreased production of perivascular reactive oxygen species (ROS) compared to vehicle-treated airways.

To improve the bioavailability of these drugs to the donor airways, we formulated these two compounds in lecithin nanoparticles. We then characterized those formulations with atomic force microscopy (AFM) and scanning electron microscopy (SEM), aided by Raman spectroscopy. Nanoparticle penetration into the trachea tissue was assessed by fluorescent confocal microscopy and mass spectroscopy of tissue sections. We lastly examined the in vivo effect of nanoparticles on airway microvascular regeneration and promotion of airway blood flow. This study demonstrated that tissue ischemia can be limited by local administration of nanoparticles designed to enhance HIF-1α expression.

Material and Methods

Preparation of Nanoparticle Formulations.

Analytical grade DFO was purchased from Sigma (St. Louis, Mo.). Lecithin was obtained from the soft-gels nutritional supplement made by Finest Natural and distributed by Walgreens. Diagnostic grade probumin was purchased from Millipore (Billerica, Mass.). All solvents used were reaction grade. To prepare the DFO dry powder, equal amounts of DFO and lecithin (48.49% each, by weight) were mixed with a 0.5% aqueous solution of probumin (3.02% by weight). The solution was stirred vigorously until a fine suspension was achieved; this suspension was then lyophilized. A control formulation containing only the vehicle was prepared by making a fine suspension of lecithin (94.14% by weight) in a 0.5% aqueous solution of probumin (5.86% by weight). The liquid suspension was then lyophilized. A nanoparticle solution was prepared by mixing the dry powders with a 1:9 (w/v) ratio of 40% propylene glycol in deionized water.

Mice.

All animal procedures were approved by Stanford's Administrative Panel on Laboratory Animal Care (APLAC) and/or the VA Palo Alto Institutional Animal Care and Utilization Committee (IACUC). All mice including C57BL/6J (B6; H-2b), Balb/C (H-2d) were purchased from Jackson Laboratory.

Scanning Electron Microscopy (SEM).

Characterization of dry powders. All fixatives used in the preparation of samples for scanning electron microscopy were obtained from Electron Microscopy Sciences (Hatfield, Pa.). Nanoparticle formulations in propylene glycol solution were drop-casted onto an SEM sample stub with a double-sided carbon tab and then air dried at room temperature. The deposited powder was then sputter-coated with an Au—Pd film (7 nm in thickness) in a Denton Desk II machine (Denton Vacuum, N.J.), and imaged with a Hitachi S-3400N VP-SEM (Hitachi High Technologies, TX), using secondary electron (SE) detection, operated at 10-15 kV.

Assessment of the Tracheal Microstructure Following Incubation in Nanoparticle Formulations.

Whole tracheas were harvested from BALB/c mice and transferred to 1xPBS on ice. The tracheas were incubated in nanoparticle solutions at 37° C. for 10 minutes in a humidified chamber. The tubular tracheal sections were rinsed in 1xPBS twice, blot dried and fixed overnight in 4% paraformaldehyde with 2% glutaraldehyde in 0.1M sodium cacodylate buffer (pH7.4). Tissues were gently washed twice with the same buffer, and then post-fixed in 1% aqueous osmium tetroxide ($OsO_4$) for one hour. Samples were then washed twice in purified water, and dehydrated in a series of increasingly concentrated ethanol rinses (50%, 70%, 90%, 100%, each rinse twice and 15 min per rinse). The specimens were finally critical-point dried (CPD) in liquid $CO_2$, in a Tousimis 815B critical point dryer (Tousimis Rockville Md.). CPD-dried samples were mounted on 45° angled SEM stubs with adhesive copper tape and sputter-coated with 4 nm of Au—Pd, as described above. Minimal contact with the tissues was ensured to avoid the destruction of the fine structures. The adventitial and mucosal layers of the sections were examined with a Zeiss Sigma field emission SEM (FESEM) (Carl Zeiss, Inc., Thornwood, N.Y.) operated at 2-3 kV, using InLens SE detection.

HPLC-MS Analysis for Drug Penetration into Tracheas.

Sample preparation. Determination of the kinetics of the chelator suspension absorption into tracheal tissue. Whole tracheas were harvested from BALB/c mice and transferred to 1xPBS on ice. Each trachea (3~4 mg dry weight) was cut evenly into 3 or 4 cross-sectional segments. Tracheal segments were then dipped in DFO formulation for 3 seconds, blot dried to remove excessive solution and incubated in a humidified chamber at 37° C. for 0, 10, 30 and 60 minutes. After incubation, the segments were rinsed in 1xPBS twice and digested in 50 μl of 0.75 mg/ml Liberase TL (Roche Applied Science, IN) in $H_2O$ at 37° C. overnight. Digested tissues were further homogenized by sonication.

Preparation of Pig and Human Trachea for Chelator Formulation Penetration Analysis.

After 4 hours incubation in DFO or DFX nanoparticle solution, pig and human trachea sections were prepared by lateral sectioning. Sections (0.5 mm each) were collected and digested with 3 volumes (v/w) of Liberase TL (0.75 mg/ml in $H_2O$) overnight at 37° C. Samples of trachea lysate were vortexed and homogenized with a probe sonicator. For all types of tracheal tissues, 50 μl of acetonitrile (100 μl) was added to the tissue homogenate to extract DFO. The samples were then centrifuged and the supernatant was diluted (1:20 to 1:100) in 50% acetonitrile and transferred to HPLC vials.

HPLC-MS/MS Analysis.

Preparation of HPLC-MS/MS standards. All chemicals and solvents for HPLC-MS/MS were purchased from Sigma (St. Louis, Mo.) or Fisher Scientific (Hampton, N.H.). Stock standard solutions of DFO were prepared by dilution of accurately weighed powders in DMSO. Calibration spiking solutions were prepared by diluting the stock solution with methanol: water (1:1, v/v) to final concentrations of 50, 20, 10, 5, 2, 1, 0.500, 0.200, and 0.100 μg/mL of DFO. Standard spiking solutions (30 μl) were added into vehicle treated tracheal section homogenates and processed with each batch of unknown samples. Chromatograms for standards were used to establish characteristic retention times (RTs) of DFO, and verified that the MS signal was linear over the range of 0.1-50 μg/ml in tracheal section homogenates. The peak areas of DFO were calculated and plotted against the concentration of the calibration standards. Calibration curves were generated using the least squares linear regression method with Analyst® 1.5.1 software.

HPLC-MS/MS Data Acquisition.

For DFO separation and detection, the flow rate was set at 300 μl/min. Chromatographic separation was performed on an Ascentics ES Cyno column (Sigma, St. Louis, Mo.). A 2.5-minute elution was performed with a 20-90% gradient of 0.1% formic acid in acetonitrile as mobile phase B; mobile phase A was 5 mM ammonium acetate/0.1% formic acid in water. After 3 minutes, % B was changed to 20% and kept for 1 minute. The HPLC was directly coupled to an AB SCIEX 4000 QTRAP triple quadrupole mass spectrometer with electrospray ionization. To monitor DFO, the mass spectrometer was operated in the positive multiple reactions monitoring mode, with transitions of 561.17/102.30 and 560.79/201.00 Da. The switching valve diverted HPLC flow to the mass spectrometer at 0.4-3 minutes. The elution time for DFO was 0.7 minutes.

HPLC-MS/MS Data Analysis.

Peak detection, integration and data processing were performed with the AB SCIEX Analyst 1.5.1 software package. Concentrations of DFO were calculated by plotting the peak area of unknown samples against the calibration curve prepared in the corresponding matrix. A 1/x weighted linear regression was used to calculate the unknown DFO concentrations.

Raman Spectroscopy and Atomic Force Microscopy (AFM) Imaging.

Both Raman and AFM were performed using NTEGRA Spectra combined AFM-Raman system (NT-MDT). For individual particle Raman scanning, dry lyophilized propylene glycol particle cluster was gently tapped against the surface of pre-cleaned Si wafers. Tissue samples for Raman scanning were made by spreading the nanoparticle solution on tissue patches (about 7×7 mm), which were fixed to the surface of glass slides and allowed to dry. Raman measurements and confocal scanning of the nanoparticles applied to either Si wafers or tracheal tissues were performed in backscattering geometry with a long-working Mitutoyo objective (100×, 0.7 NA). The illumination light was 473 nm, and the power was kept at ~0.8 mW to minimize sample damage. Raman maps were produced with a step size of 0.5 µm and 1 s exposure. 600 gr/mm gratings were used for optimal signal and spectral resolution.

AFM imaging was performed in tapping mode with commercial cantilevers (k=5.4 N/m, R<10 nm) at 0.7 Hz. This provided surface topography and phase contrast images to discern stiffness of different areas within the islands. The locally equalized topography image was also obtained from the initial topography image by the AFM image analysis software, supplied with the instrument, to allow taller structures to be seen.

Analysis of Nanoparticle Cellular Localization.

Rhodamine B isothiocyanate (RBITC) was purchased from Sigma; 1,2-distearoyl-sn-glycero-3-phosphoethanolamine—poly(ethylene glycol)—amine (DSPE-PEG-NH2, Mw=3400) was purchased from Laysan Bio (Arab, Ala.) and the PD-10 desalting column was purchased from GE Healthcare. Rhodamine, a fluorescent marker, was linked to an inert lipid (DSPE) in the nanoparticle formulation. The linking reaction was performed by dissolving 34 mg (10 µM) of DSPE-PEG-NH2 and 15.6 mg (29.1 µM) of RBITC in a 1 ml solution of methanol:water (1:9, v/v). The reaction mixture was stirred overnight in a dark room at 4° C. The solution was then run through a PD-10 desalting column with MilliQ water to remove the unreacted RBITC. The labeled fractions were collected and lyophilized to obtain rhodamine-labeled DSPE. To prepare the fluorescent labeled nanoparticles, DSPE was mixed with 1% lecithin by weight. The labeled nanoparticles were administered on the inside and outside of the walls of tracheal samples, and then incubated at 37° C. for 4 hours. After incubation, they were washed 3 times with PBS, then embedded in OCT (Sakura Finetek) to make frozen sections. The tissue blocks were cut to 20 µm sections. Samples were stained with mounting media containing DAPI fluorescent dye and imaged with a Leica SP2 confocal fluorescence microscope.

Tracheal Transplantation.

Four to six week old BALB/c mice were used as donors and age and sex matched B6 mice were used as recipients. The surgical procedure of orthotopic tracheal transplantation was performed as previously described (see Jiang et al. (2011) *J Clin Invest* 121:2336-2349). Briefly, both donor and recipient mice were anesthetized with 50 mg/kg of ketamine and 10 mg/kg of xylazine. 5- to 7-ring tracheal segments were removed from donor mice. The donor tracheas were stored in PBS on ice prior to transplantation. A ~2-3 cm incision was made in the midline of the recipient's neck. The strap muscles were then bluntly dissected and retracted with 3-0 suture to allow clear exposure of the laryngotracheal complex. After the recipient trachea was transected, the donor graft was removed from the PBS, blot dried and then soaked in the chelator suspension for approximately 5 seconds. The trachea was removed of the solution and blot dried again to remove excess chelator suspension. The trachea was then sewn in with 10-0 nylon suture as previously described. Then, ~100 µl of chelator suspension was applied to the outer wall of the donor trachea and anastomoses. The skin was closed with 5-0 silk sutures.

Blood Perfusion Monitoring by Laser Doppler Flowmetry.

The procedure has been described in detail in Khan et al. (2012) *Am J Physiol Lung Cell Mol Physiol* 303:L861-869. In short, the transplanted mice were placed under general anesthesia and the tracheal grafts were carefully exposed using stay sutures to gently retract the strap muscles, revealing the anterior wall of the trachea. Perfusion monitoring was performed with a fiberoptic LDF probe connected to the OxyLab laser Doppler flowmetry (LDF) monitor (Oxford Optronix). This provides a continuous digital readout of blood perfusion units (BPUs) by real-time measurements of red blood cells in flux that is proportional to the red blood cell perfusion. The probe is connected to a micromanipulator and is gently lowered onto the outer surface of tracheal grafts and BPU measurements were recorded.

Tissue Preparation for Perfusion Studies and Immunohistochemistry.

For whole-mount tracheal microvascular analysis, mice were injected with 100 µl of FITC-conjugated tomato lectin (Vector Laboratories) at a concentration of 1 mg/ml. After 5 minutes of circulation, the mice were perfused with 1% PFA diluted in PBS for about 2 minutes until the outflow of the solution turned clear. The tracheas were then harvested, fixed in 1% PFA for 1 hour at 4° C., and then washed 3 times with PBS. Whole tracheas were mounted on glass slides in Vectashield H-1200 mounting medium (Vector Laboratories). Assessment of the percentage of the perfused area was carried out as previously described. Briefly, the whole tracheal allograft (every cartilaginous and inter-cartilaginous region) was examined and each area was scored either a 1 if it was perfused or 0 if it was not perfused. The percent perfusion was then calculated as follows: total score/total regions examined. Frozen sections were used for other immunohistochemistry analysis. Tracheal samples were snap-frozen in OCT solution (Sakura Finetek) and the samples were stored at −80° C. 8-µm sections were used for immunofluorescence staining. Anti-CD31 antibody (1:200; BD Pharmingen) was used to stain endothelial cells; anti-Ki67 antibody (1:100; BD Pharmingen) was used to stain proliferating cells; anti-p-eNOS antibody (1:100; Cell Signaling) was used to stain phosphorylated form of eNOS in endothelial cells. Dihydroethidium (DHE) (20 µM, Invitrogen) was used to detect reactive oxygen species (ROS). The TUNEL assay (Invitrogen, C10245) was carried out according to the manufacturer's protocol. Photomicrographs were taken with a Zeiss LSM 510 laser scanning confocal microscope with a Zeiss LSM Image Browser software. Quantification of the staining of Ki67, p-eNOS, dihydroethidium and TUNEL were performed with ImageJ software.

Quantitative Real Time RT-PCR.

Tracheal samples were incubated in RNAlater solution (Invitrogen) overnight at 4° C. Total RNA was then isolated using the QIAGEN Shredder and RNeasy Mini Kit (QIAGEN) as per the manufacturer's protocol. Total RNA (1 µg) was reverse transcribed with Moloney murine leukemia virus reverse transcriptase (Invitrogen) and 5 µM random hexamer primers according to the manufacturer's protocol. 2 µl of 1:10 diluted reverse transcription reactions were added to quantitative real time-PCR (qRT-PCR) reactions with 5 µl of 2×SYBR Green Master Mix (Applied Biosystems) and 100 nM of forward and reverse primers specific for the genes of interest in a total volume of 10 µl. Detection was carried out with the ABI Prism 7700 sequence detector (Applied Biosystems). SDS analysis software (Applied Biosystems) was used to analyze the data. Cyclophilin mRNA expression was used to normalize gene expression to account for sample-to-sample variation in input and reverse transcription efficiency. The $2^{-\Delta\Delta C_t}$ method was used to calculate fold changes.

Statistics.

Statistical analysis was performed using 2-tailed Student's t test, with a significance level of p<0.05.

Results

Structure and Morphology Analysis of Drug Nanoparticles.

DFO was formulated into encapsulated drug nanoparticles and drug powders. Tracheal membrane-compatible lecithin was selected to encapsulate the drugs to ensure their efficient delivery to the tissue. To assess the encapsulation efficiency, structural analysis of DFO before and after encapsulation was performed using Raman spectroscopy. A Raman spectrum of pure DFO was first examined (FIG. 1B). DFO molecules in the nanoparticle exhibited a spectrum different from that of pure DFO, with many bands merging together and becoming broader, which was likely due to strong hydrodynamic screening of DFO molecules and the disruption of its crystalline structure (FIG. 1C).

Next, SEM was used to study the morphology of the nanoparticles. To acquire SEM images of dry nanoparticle powder, 40% propylene glycol was first used to make the nanoparticle solution which was then deposited onto generic aluminum SEM sample stubs and air-dried in situ. The blank vehicle showed a generally homogeneous lecithin structure (FIG. 1D), and DFO nanoparticles also showed homogeneous semi-porous networks (FIG. 1E).

Chelator Nanoparticle Homogeneity.

Figure 2B:
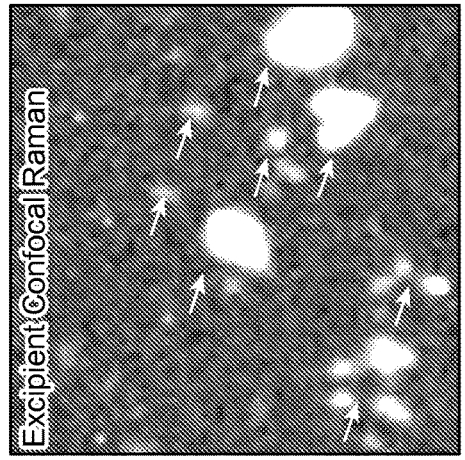
Figure 2C:
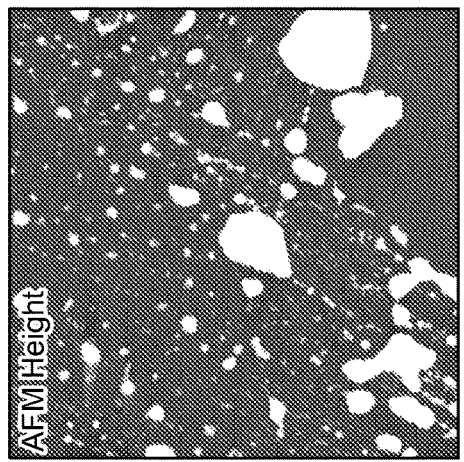
Figure 2D:
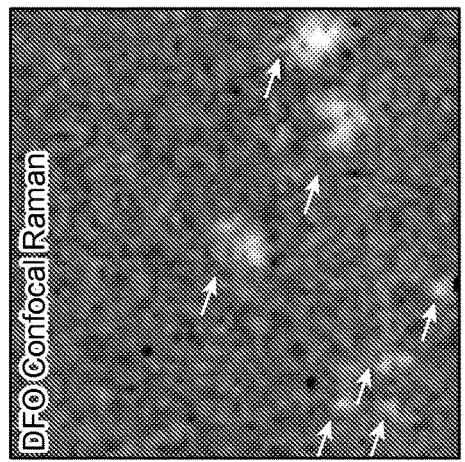
Figure 2E:
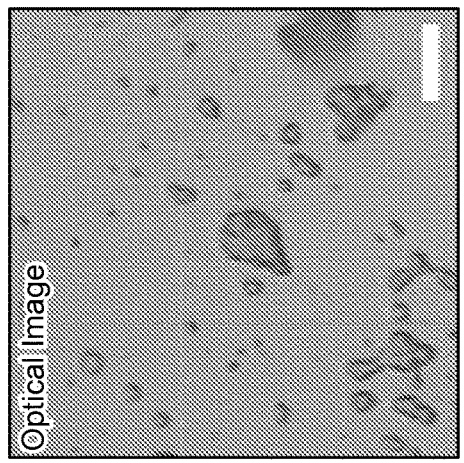
Figure 2F:
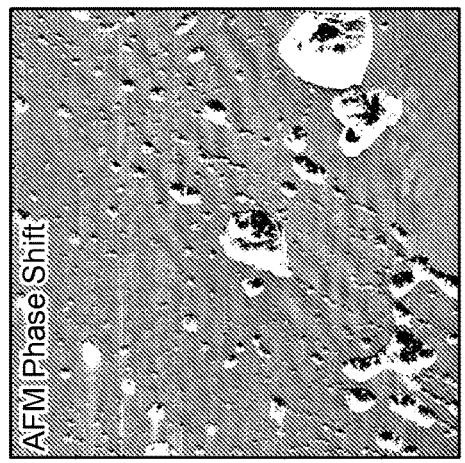

To determine the degree of homogeneity in the distribution of DFO within the nanoparticle, confocal Raman scanning and AFM imaging of small nanoparticle islands on the surface of Si wafers was performed. Sample material was loaded onto the surface of Si wafer to ensure the acquisition of high quality images, and imaging was performed under low power (<1 mW) to avoid sample damage. The optical image of DFO showed that the surface was covered by separate islands (FIG. 2A). The inner structure of the islands was probed by AFM scanning in tapping mode. AFM images showed the morphology and size of smallest nanoparticles, as well as larger nanoparticle aggregates (FIG. 2B-D). Confocal Raman images showed uniform distribution of the excipient and the DFO nanoparticle formulation as well as very good correlation between the distribution of DFO and excipient (FIG. 2E, F). These data together demonstrate that DFO was efficiently encapsulated in the excipient lecithin.

Microstructure Analysis of Chelator Treated Trachea.

Although the main ingredients used in the nanoparticle formulation are considered safe, we wanted to confirm that the administration of the nanoparticles on the tracheal surface would not adversely affect tracheal microstructures. SEM was used to examine the morphology of the nanoparticle-treated tracheas. The images showed that the adventitial layer of the tracheas treated with vehicle or DFO solution were not significantly different from that of the untreated samples. Similar to the untreated tracheal samples, individual collagen fibrils displayed fine structures with lateral rings clearly visible (FIG. 9A). Also, the mucosal layer of the tracheas treated with vehicle or nanoparticles did not show any visible signs of damage (FIG. 9B). Only a few brushes were observed to be missing from the tops of some cilia bundles in treated samples; a finding likely caused by the capillary forces exerted by water during the nanoparticle solution washing process. Altogether, our data suggest that a 10 min incubation of tracheas in the nanoparticle formulation did not significantly affect the microstructure of the airway.

Drug Penetration into the Tracheal Tissue.

Figure 3A:
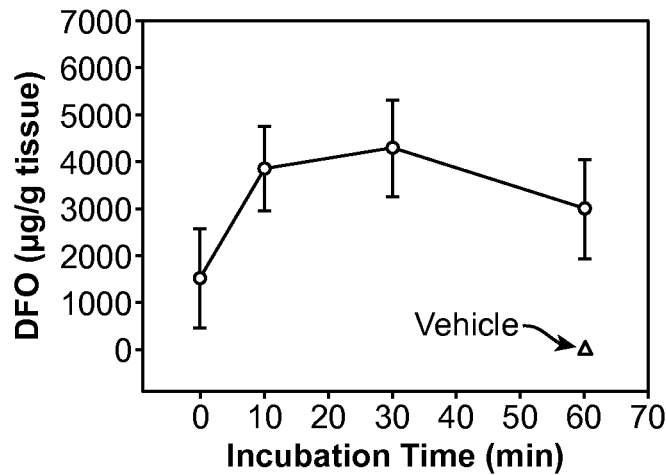
Figure 3B:
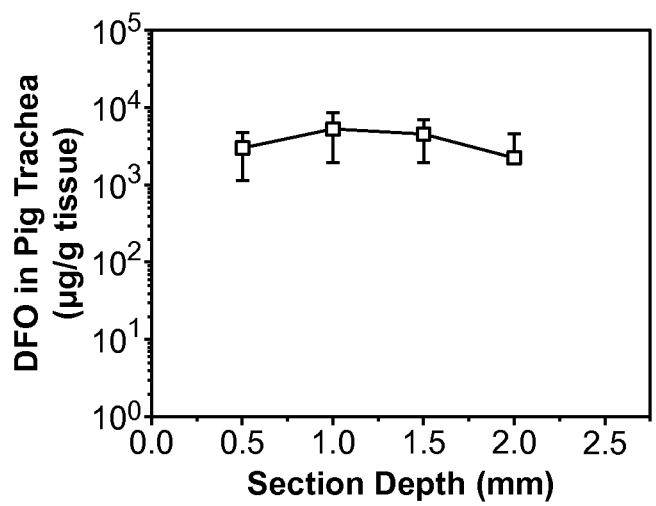
Figure 3C:
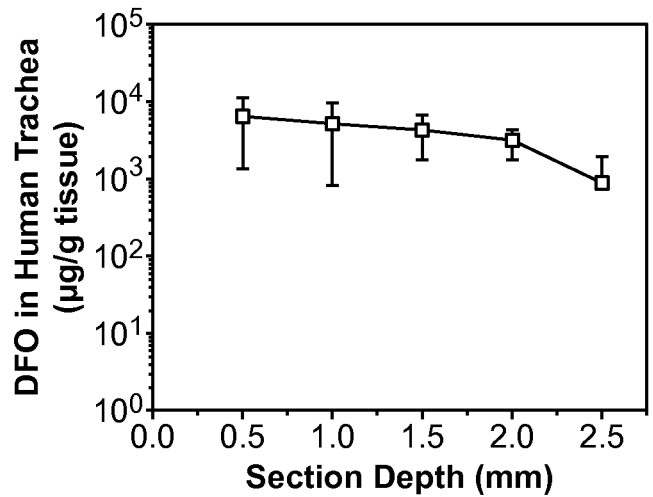

We next assessed the drug nanoparticle penetration into the tracheal tissue. Examination of the penetration kinetics showed that the DFO nanoparticle achieved near-maximum penetration at 10 min of incubation, and reached a plateau when approaching 60 min (FIG. 3A). We then determined the depth of drug penetration and absorption by HPLC-MS/MS. Because mouse tracheas are relatively thin, we chose to use pig and human tracheas for these studies. Although the efficiency of penetration was variable, DFO nanoparticles were able to penetrate the pig and human tracheas (FIG. 3B, C). In the pig trachea, DFO penetrated to and was absorbed to a depth of 2 mm (FIG. 3B). A similar trend was also observed in the human trachea penetration depth analysis (FIG. 3C). These data suggest that the penetration of DFO is efficient in both species of mammalian tracheas examined.

Drug Penetration into Cytoplasm of the Tracheal Cells.

Figure 4C:
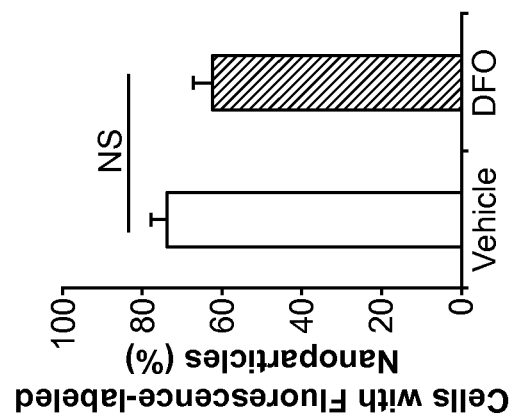
Figure 4B:
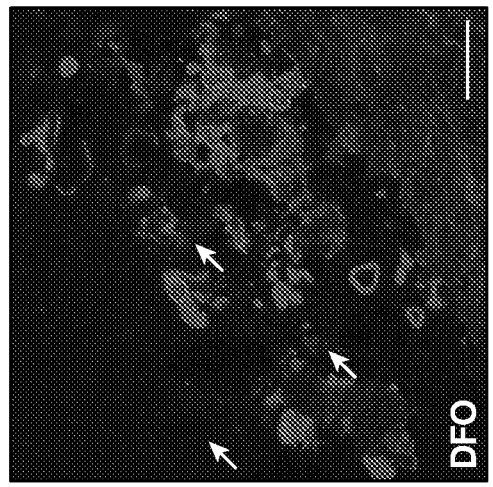
Figure 4A:
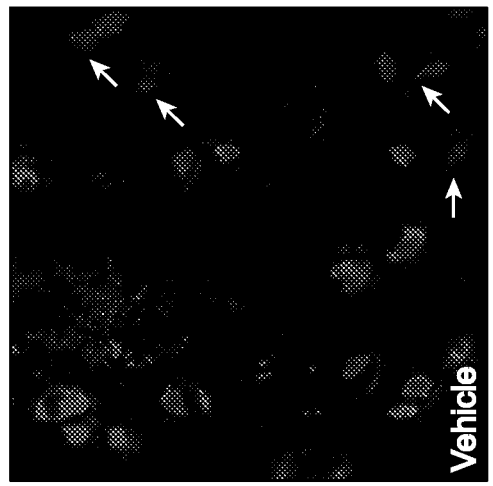

To test the efficacy of drug absorption, we used confocal microscopy to determine the cellular localization of the drug nanoparticles. Because cells of the subepithelial layer play a more important role in angiogenesis, we examined the penetration of drug into these cells. Fluorescence-tagged vehicle was found to be localized in the cytoplasm of cells in tracheas treated with vehicle or DFO nanoparticles (FIG. 4A, B). Quantification showed that the percentages of fluorescence-positive cells were about 70% and 60% for the vehicle and DFO formulation respectively (FIG. 4C). Because the drugs were previously shown to be well-encapsulated by the vehicle (FIG. 1E), the fluorescence signal can be used to estimate the cellular localization of the drug molecules. These images confirmed that the DFO nanoparticle formulation efficiently penetrated the tissue and reached the cells in the subepithelial layer of the trachea.

Effects of DFO Chelator on Microvascular Anastomosis Formation and Airway Microvascular Perfusion.

The mouse OTT model has been shown to faithfully replicate lymphocytic bronchitis observed in lung transplant recipients, and is useful for studying phenomena associated with clinical airway complications. We have previously shown that the airway microvascular circulation can be easily studied in this model and that the perfusion of the airway allograft can be used to assess the regeneration of the injured airway microvasculature, particularly at the anastomosis. The airway allograft is transplanted en bloc, and there is no vascular perfusion prior to the formation of the microvascular anastomosis between the graft donor and the recipient. Therefore, earlier (i.e. day (d) 3 following transplantation) appearance of graft perfusion indicates an accelerated vascular anastomosis formation. In this model, airway perfusion loss around d10 is consistently observed and is primarily caused by alloimmune-mediated endothelial cells injury as previously described by Babu et al. (2007) *J Clin*

*Invest* 117:3774-3785. Thus, persistent airway microvascular perfusion at d10 indicates more efficient repair of damaged vessels. FITC-lectin microvascular perfusion images showed that DFO treatment significantly increased airway perfusion at both d3 and d10 following transplantation (FIG. 5A), and the microvascular perfusion of vehicle treated allografts was not significantly differently from non-treated control transplants (FIG. 5A). Percentages of perfused areas of trachea allografts treated with DFO were >90% in contrast to <20% in control and vehicle treated airways at both d3 and d10 (FIG. 5B). The use of LDF for transplanted tracheal tissue blood perfusion was recently developed by our laboratory and has been previously used to assess airway perfusion. LDF showed that perfusion of the allograft treated with DFO was significantly higher at both d3 and d10 compared to control and vehicle treated grafts (FIG. 5C). These studies suggest that DFO nanoparticles accelerated airway microvascular anastomosis formation and promoted the repair of damaged vasculature.

Effects of DFO Nanoparticle on Angiogenic Factor Expression in Ischemic Airways.

We next asked how DFO promotes airway microvascular perfusion. Expression of angiogenic factors and cytokines are closely associated with neovascularization. Based on the observation that the promotion of vascular perfusion by DFO was most significant at d3 following transplantation, we isolated mRNA from d3 allografts and analyzed the expression of angiogenic factors and cytokines (PLGF, SDF-1, VEGF, ANGPT1 and ANGPT2) and the angiogenic receptor, Tie2 by quantitative real time RT-PCR. Expression of PLGF and SDF-1 was significantly increased (FIG. 6A, B), but there was no significant difference observed in the expression of angiogenic factors, VEGF, ANGPT1 and ANGPT2 or the Tie2 receptor (FIG. 6 C-F). Consistent with the results of the mRNA study, immunofluorescent staining showed that the levels of PLGF and SDF proteins were also increased (FIGS. 10 A and B). These data suggest that DFO likely promotes early microvascular anastomosis formation through the upregulation of angiogenic growth factors.

Effects of DFO Nanoparticles on Tracheal Endothelial Cells.

Endothelial nitric oxide synthase (eNOS) phosphorylation is associated with endothelial cell survival and angiogenesis. We hypothesized that DFO may increase eNOS phosphorylation in this transplantation model system. Examination of endothelial phosphorylated eNOS (p-eNOS) expression in d3 allograft showed that DFO treatment increased p-eNOS expression by about 2 fold (FIG. 7A, B). EC proliferation, measured by Ki67 staining, in DFO treated allografts was much higher than that of the vehicle treated samples (about 30% vs 15%) (FIG. 7C, D). Production of ROS in ischemic tissue is associated with EC death. Dihydroethidium (DHE) staining showed that DFO treated allograft exhibited much lower levels of perivascular ROS production (FIG. 8A, B). Lastly, the TUNEL assay showed that DFO treatment significantly decreased EC apoptosis (FIG. 8C, D). These data together suggested that DFO may also improve airway microvascular perfusion by augmenting angiogenesis through the promotion of EC proliferation and prevention of EC apoptosis.

The biophysical properties of DFO nanoparticles were characterized by utilizing various techniques. Raman spectroscopy structure analysis and imaging showed that DFO encapsulation by lecithin was very efficient. Next, the SEM morphological study of the dry nanoparticle powder showed that the DFO formulation was also homogeneous. Lastly, confocal microscopy showed a very high percentage of drug-positive cells in tracheas treated with the DFO nanoparticles. Consistent with these, in vitro identified superior biophysical properties, the DFO nanoparticles were highly effective in promoting airway microvascular perfusion. Nanoparticles with more efficient encapsulation, better tissue penetration and retention are likely to display higher bioactivity in vivo.

Airway ischemia has also been shown to be a risk factor for anastomotic bacterial and fungal overgrowth, which often further increases the risk of the development of airway complications. We recently demonstrated that *Aspergillus fumigatus* airway invasion could be attenuated in transplant recipients with genetically-upregulated HIF-1α levels that resulted in better airway allograft perfusion. These data together suggest that DFO nanoparticles may limit airway complications through alleviating tissue ischemia and diminishing relevant microbial infection.

DFO is a bacterial siderophore produced by the Actinobacteria *Streptomyces pilosus*. Because DFO depletes iron, it is generally used as an iron-chelating drug to treat iron overload conditions. Recent studies suggest that, DFO also promotes angiogenesis and alleviates tissue ischemia in animal models. This property of DFO is generally thought to be due to its ability to stabilize HIF-1α through the inhibition of prolyl 4-hydroxylase by chelation of iron from enzyme's catalytic center.

We found that DFO treated airway grafts expressed significantly higher levels of PLGF and SDF-1, but no significant difference was noted in the expression of VEGF, ANGPT1 and ANGPT2. The increase in expression levels of PLGF and SDF-1 with DFO is consistent with our previous study utilizing adenovirus-mediated HIF-1α gene therapy. HIF-1 activates transcription of the gene encoding SDF-1, and increased SDF-1 expression promotes vascular regeneration by enhancing recruitment of CXCR4-expressing angiogenic cells. While other studies have shown that VEGF is often upregulated following DFO treatment, the DFO nanoparticles in this study did not increase VEGF expression in d3 allografts. It is likely that PLGF, like SDF1, serves as a chemotactic factor for the recruitment of bone marrow-derived angiogenic cells. PLGF is a member of the VEGF family of growth factors, but unlike VEGF, PLGF is not required for vascular development and homeostasis; PLGF has diverse non-redundant roles in various physiological or pathological status such as tissue ischemia, inflammation and malignancy. PLGF is also considered a protective paracrine effector in the heart and was recently shown to promote myocardial blood flow and contractile function in chronic myocardial ischemia by increasing neovascularization. PLGF has also been shown to enhance endothelial cell proliferation, migration and survival. Consistent with these studies, we observed increased expression of Ki67 in DFO nanoparticles treated tracheal endothelial cells, supporting the notion that, in this airway transplantation model, PLGF may promote airway anastomotic microvascular formation through stimulating endothelial cell proliferation and subsequent angiogenesis.

DFO treatment significantly increased the levels of the p-eNOS. eNOS is activated/phosphorylated by the PI3K-Akt pathway. Interestingly, PLGF has been shown to enhance Akt activation in endothelial cells to promote their proliferation and migration and has also been shown to activate Akt in monocytes. Recent studies showed that PLGF is a direct HIF target gene and that it dilates mesenteric arteries through NO production. It is therefore likely that, in this airway transplantation model, DFO increased p-eNOS through PLGF activated PI3K-Akt pathway.

ROS are known to cause endothelial cell dysfunction, and increased ROS production promotes eNOS uncoupling, which is a significant contributor to oxidative stress. Iron participates in the redox reactions that lead to the production of ROS, and the reduction of ROS by iron chelation has been shown to be an effective therapy for atherosclerosis. These studies suggest that endothelial cell damage may be promoted by a feed-forward cycle of eNOS dysfunction leading to ROS production which leads to further eNOS dysfunction. In airways treated with DFO, we observed a reduction in ROS production concomitantly with increased levels of p-eNOS; this finding suggests that through its iron-chelating activity, DFO may prevent or at least ameliorate endothelial cell injury through reducing oxidative stress by enhancing the function of eNOS. In summary, DFO augmented airway anastomotic microvascular regeneration through the production of angiogenic factors as well as reduction of ROS, which improved overall endothelial cell health and decreased airway ischemia.

What is claimed is:

1. A method of improving clinical outcome in an individual following lung transplantation, the method comprising:
   directly contacting a bronchial passage of the individual, in a rejection episode following transplantation, with an effective dose of a nanoparticle formulation comprising an effective dose of an iron chelating agent;
   wherein ischemia and hypoxia at the contacted surface is reduced and clinical outcome is improved.

2. The method of claim 1, wherein the contacting step is performed by pulmonary inhalation of an aerosol formulation.

3. The method of claim 2, wherein the iron chelator is selected from deferoxamine (DFO), deferasirox (DFX), and deferiprone (DFP).

4. The method of claim 3, wherein the iron chelator is DFO.

5. The method of claim 2, wherein the nanoparticle is comprised of the iron chelating agent and a pharmaceutically acceptable stabilizer.

6. The method of claim 5, wherein the iron chelator comprises from about 5% to about 75% of the total weight of the nanoparticle.

7. The method of claim 6, wherein the iron chelator comprises from about 40% to about 60% of the total weight of the nanoparticle.

8. The method of claim 5, wherein the stabilizer comprises cationic lipids.

9. The method of claim 5, wherein the stabilizer comprises phospholipids.

10. The method of claim 5, wherein the stabilizer comprises lecithin.

11. The method of claim 5, wherein the stabilizer further comprises protein.

12. The method of claim 11, wherein the stabilizer comprises a mixture of protein, and a cationic lipid in a ratio of from about 1:15 to 1:5 by weight.

13. The method of claim 5, wherein the nanoparticles are formed by precipitation of the iron chelating agent and pharmaceutically acceptable stabilizer from a liquid suspension.

14. The method of claim 5, wherein the nanoparticles have a diameter of from about 10 nm to about 5 µm.

15. The method of claim 14, wherein the nanoparticles have a diameter of from about 100 nm to about 5 µm.

16. The method of claim 5, wherein the nanoparticles are formulated by suspension in a physiologically acceptable carrier.

17. The method of claim 1, wherein the formulation is provided in a container and carrier for generation of an aerosol.

* * * * *